US009833374B2

(12) United States Patent
Oshima et al.

(10) Patent No.: US 9,833,374 B2
(45) Date of Patent: Dec. 5, 2017

(54) TRAINING APPARATUS

(71) Applicants:Murata Machinery, Ltd., Kyoto-shi, Kyoto (JP); Teijin Pharma Limited, Chiyoda-ku, Tokyo (JP)

(72) Inventors: Osamu Oshima, Kyoto (JP); Hiroaki Ohmatsu, Kyoto (JP); Akihiro Maeda, Chiyoda-ku (JP); Fumi Fujita, Chiyoda-ku (JP); Jun Takeda, Chiyoda-ku (JP)

(73) Assignees: MURATA MACHINERY, LTD., Kyoto (JP); TEIJIN PHARMA LIMITED, Tokyo (JP)

( * ) Notice: Subject to any disclaimer, the term of this patent is extended or adjusted under 35 U.S.C. 154(b) by 44 days.

(21) Appl. No.: 15/036,587

(22) PCT Filed: Nov. 12, 2014

(86) PCT No.: PCT/JP2014/079949
§ 371 (c)(1),
(2) Date: May 13, 2016

(87) PCT Pub. No.: WO2015/072479
PCT Pub. Date: May 21, 2015

(65) Prior Publication Data
US 2016/0287462 A1    Oct. 6, 2016

(30) Foreign Application Priority Data
Nov. 14, 2013   (JP) .................................. 2013-235816

(51) Int. Cl.
*A61H 1/02*    (2006.01)
*A61B 5/11*    (2006.01)
(Continued)

(52) U.S. Cl.
CPC .......... *A61H 1/0237* (2013.01); *A61B 5/1122* (2013.01); *A61B 5/1124* (2013.01);
(Continued)

(58) Field of Classification Search
CPC ....... A61H 1/02–1/0214; A61H 1/237–1/0288
See application file for complete search history.

(56) References Cited

U.S. PATENT DOCUMENTS 5,211,161 A * 5/1993 Stef ..................... A61H 1/0266
601/31
9,554,966 B2 * 1/2017 Kuro .................... A61H 1/0274
(Continued)

FOREIGN PATENT DOCUMENTS

JP   2000-189475 A   7/2000
JP   2005-118466 A   5/2005
(Continued)

OTHER PUBLICATIONS

English language translation of International Search Report dated Dec. 16, 2014 issued in corresponding PCT application PCT/JP2014/079949.
(Continued)

*Primary Examiner* — Valerie L Woodward
(74) *Attorney, Agent, or Firm* — DLA Piper LLP (US)

(57) ABSTRACT

A training apparatus includes a fixed frame, a training rod, a motor, rotation information detection sensor, tilt angle and position difference calculation units, determination, motor drive and position difference eliminating units. The training rod is supported by the fixed frame in a manner capable of being tilted by a motor about at least an X-axis or a Y-axis so as to hold the limb. The tilt angle calculation unit calculates a tilt angle of the training rod. The position difference calculation unit calculates a position difference. The determination unit obtains the position difference every
(Continued)

time when a second time period elapses. If the position difference generated in the second time period is a first threshold or lower, the motor drive unit drives the motor so that the position difference is accumulated and maintained. The position difference eliminating unit resets the position difference at a predetermined timing.

12 Claims, 21 Drawing Sheets

(51) Int. Cl.
*A63B 21/00* (2006.01)
*A63B 21/005* (2006.01)
*A63B 23/035* (2006.01)
*A63B 23/12* (2006.01)
*A63B 24/00* (2006.01)
*G06F 19/00* (2011.01)
*A63B 71/06* (2006.01)

(52) U.S. Cl.
CPC ....... *A61H 1/0274* (2013.01); *A63B 21/0058* (2013.01); *A63B 21/00072* (2013.01); *A63B 21/00178* (2013.01); *A63B 21/4017* (2015.10); *A63B 21/4033* (2015.10); *A63B 21/4035* (2015.10); *A63B 21/4047* (2015.10); *A63B 23/03508* (2013.01); *A63B 23/1281* (2013.01); *A63B 24/0006* (2013.01); *A63B 24/0062* (2013.01); *A63B 24/0087* (2013.01); *G06F 19/3481* (2013.01); *A61B 2505/09* (2013.01); *A61H 2201/1207* (2013.01); *A61H 2201/1215* (2013.01); *A61H 2201/1659* (2013.01); *A61H 2201/5035* (2013.01); *A61H 2201/5038* (2013.01); *A61H 2201/5043* (2013.01); *A61H 2201/5046* (2013.01); *A61H 2201/5048* (2013.01); *A61H 2201/5061* (2013.01); *A61H 2201/5064* (2013.01); *A61H 2201/5069* (2013.01); *A61H 2201/5084* (2013.01); *A63B 23/0355* (2013.01); *A63B 71/0622* (2013.01); *A63B 2024/0071* (2013.01); *A63B 2024/0093* (2013.01); *A63B 2208/0247* (2013.01); *A63B 2220/13* (2013.01); *A63B 2220/20* (2013.01); *A63B 2220/30* (2013.01); *A63B 2220/31* (2013.01); *A63B 2220/34* (2013.01); *A63B 2220/40* (2013.01); *A63B 2220/51* (2013.01); *A63B 2230/436* (2013.01)

(56) References Cited

U.S. PATENT DOCUMENTS

2006/0293617 A1* 12/2006 Einav .................. A61H 1/0274
601/33
2009/0227911 A1* 9/2009 Srivastava ............ A61H 1/024
601/34

FOREIGN PATENT DOCUMENTS

JP   2005-348779 A    12/2005
WO   2012-117488 A1    9/2012

OTHER PUBLICATIONS

International Preliminary Report on Patentability dated May 17, 2016, issued on corresponding International application No. PCT/JP2014/079949.

* cited by examiner

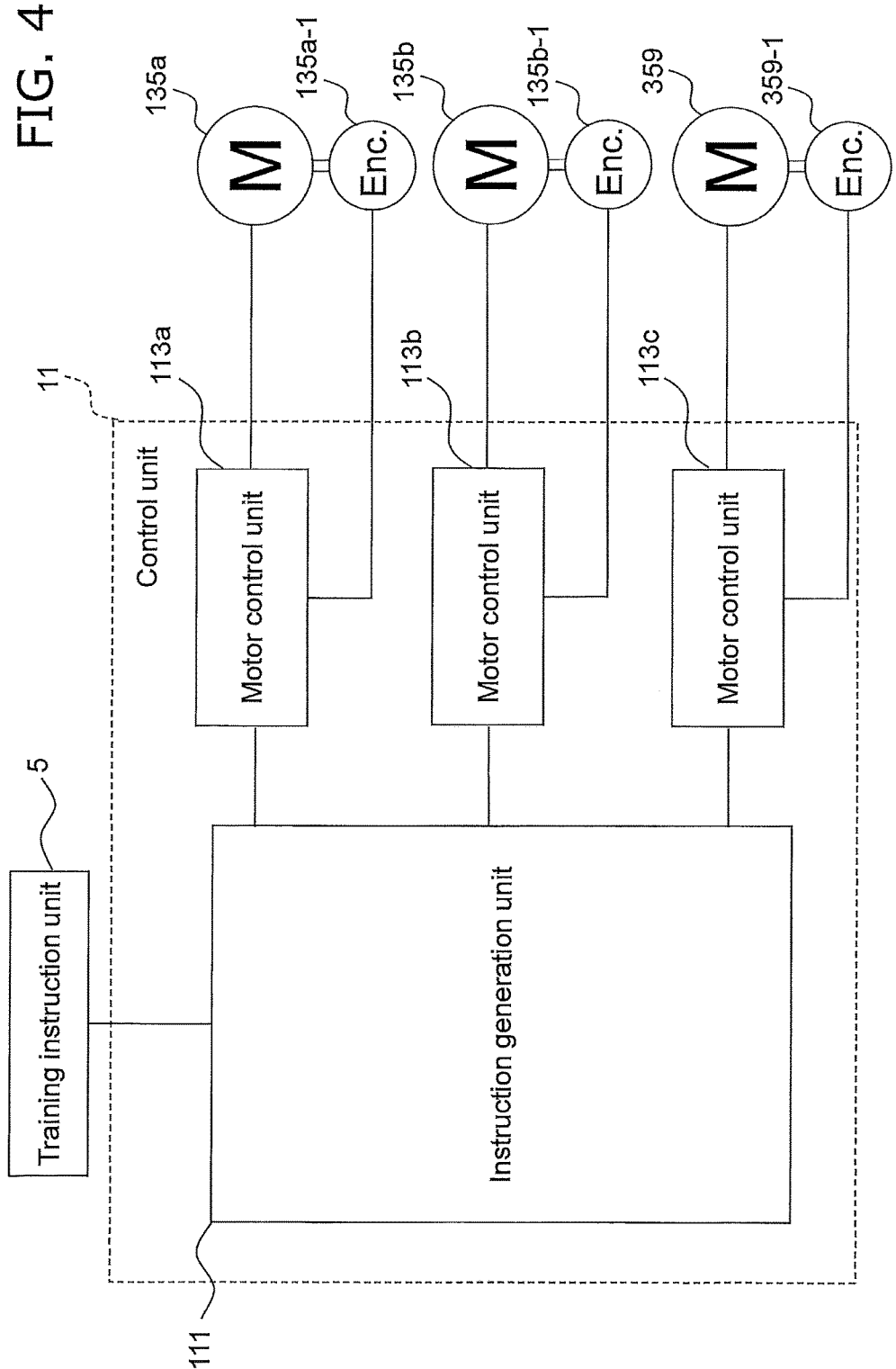

TRAINING APPARATUS

CROSS REFERENCE TO RELATED APPLICATIONS

This application is a national stage of international application no. PCT/JP2014/079949, filed on Nov. 12, 2014, and claims the benefit of priority under 35 USC 119 of Japanese application no. 2013-235816, filed on Nov. 14, 2013, both of which are incorporated herein by reference in their entirety.

TECHNICAL FIELD

The present invention relates to a training apparatus equipped with a training rod driven by a motor, for supporting rehabilitation of upper and/or lower limbs of a patient according to a predetermined training program.

BACKGROUND ART

Rehabilitation aimed at motor function recovery of upper and/or lower limbs of a stroke patient with hemiplegia is usually performed by an occupational therapist or a physical therapist, and hence there is a limitation in efficient offering of rehabilitation. For instance, in rehabilitation aimed at motor function recovery of an upper limb, it is mainly required to repeat as much as possible a correct movement of the paralyzed upper limb passively and actively in a movement range slightly larger than current range. On the basis of the rehabilitation for the motor function recovery, the occupational therapist or the physical therapist teaches the correct movement to the patient and manually applies a load on the upper limb of the patient so as to induce an active movement.

In this rehabilitation, the number of repetitions is limited due to exhaustion of the therapist. In addition, there may be a difference of medical quality of the rehabilitation depending on experience of the therapist. Accordingly, in order to support the training by the therapist, to eliminate the limitation due to exhaustion, and to standardize the medical quality as much as possible, there is known a training apparatus as described in Patent Citation 1, for example, which supports rehabilitation of a patient with a disabled limb such as an arm. The apparatus is disclosed as an upper limb training apparatus including a fixed frame that can be placed on a floor, a movable frame supported by the fixed frame so as to be capable of tilting in all directions, and a training rod attached to the movable frame in an expandable/contractible manner so as to be operated by a person who undergoes the training.

PRIOR ART CITATIONS

Patent Citation

Patent Citation 1: PCT publication No. 2012/117488

SUMMARY OF INVENTION

Technical Problem

The training apparatus as disclosed in Patent Citation 1, mainly in a case where a person who undergoes a training trains a limb, for example, an upper limb to be trained in accordance with a training program, monitors whether or not the movement of the upper limb is following the movement of the training rod, and teaches the movement of the training rod to the user of the training apparatus, as necessary, on the basis of visual or auditory information. In this case, the conventional training apparatus evaluates whether or not the movement of the upper limb is following the movement of the training rod instructed by the training program, by a calculation operation inside the apparatus, for example, on the basis of only a level of difference (a position difference) between an angle to tilt the training rod instructed by the training program and an actual tilt angle of the training rod. However, by only this evaluation method based on a level of position difference, the following status change of the position difference may not appropriately be evaluated.

In the training apparatus for training a limb, as the state in which the limb is following a movement instructed by the preset training program in the training apparatus (a following status), there are following three states.

(i) The training rod moving the limb is operated in a state where a tilt angle of the training rod is the same as that instructed by the training program (a state where the position difference is zero).

(ii) The training rod is operated in a state where the tilt angle change of the training rod per unit time is the same as a tilt angle change of the training rod instructed by the training program (a state where the position difference is not zero but is a constant value without change).

(iii) The training rod is operated in a state where the tilt angle of the training rod is gradually shifted from a tilt angle of the training rod instructed by the training program (a state where the position difference is gradually changed).

When evaluating the following status on the basis of only a level of the position difference, the following status can be evaluated in the case (i) described above, while the following status may not be correctly evaluated in the case (ii) or (iii) described above. For instance, if the position difference is not changed and is a predetermined value or larger, or if the position difference is gradually changing and becomes a predetermined value or larger, the limb movement is evaluated to be following the training program although some delay exists due to the position difference.

On the other hand, if the following status is evaluated on the basis of only a level of the position difference without considering a temporal change, in some cases of a level of the position difference, the limb movement is evaluated not to be following the training program even in the case (ii) or (iii), and hence a state of the patient corresponding to the status of the training rod cannot be appropriately monitored.

In other words, if the following status of the training rod is evaluated on the basis of only a level of the position difference, an operating status of the training rod operated by the patient cannot be appropriately determined, which is, for example, a following status in which the position difference is not zero but is not changed (a state where a constant load is applied while the training rod is moving at a constant speed), or a following status in which the position difference changes gradually (a state where the position difference gradually increases as the training rod approaches a target point). For this reason, the state of the patient cannot be appropriately monitored.

Accordingly, it is an object of the present invention to provide a training apparatus for rehabilitation support, which appropriately determines the following status where the position difference is not zero but is not changed, or the following status where the position difference gradually changes, and controls the training rod so that training of a limb is continued in the two following statuses if it is determined that the training can be continued as a result of the determination.

Technical Solution

As means for solving the problem, a plurality of embodiments are described below. These embodiments can be arbitrarily combined as necessary.

A training apparatus according to an aspect of the present invention is a training apparatus for training upper and/or lower limbs of a user in accordance with a predetermined training program. The training apparatus includes a fixed frame, a training rod, a motor, a rotation information detection sensor, a tilt angle calculation unit, a position difference calculation unit, a determination unit, a motor drive unit, and a position difference eliminating unit. The fixed frame is placed on or in the vicinity of a floor. The training rod is supported by the fixed frame in a manner capable of tilting about a predetermined tilting axis with at least one degree of freedom. In addition, the training rod holds a limb. The motor tilts the training rod about the tilting axis. The rotation information detection sensor outputs an amount of rotation of the motor. The tilt angle calculation unit calculates a tilt angle of the training rod on the basis of the amount of rotation of the motor. The position difference calculation unit calculates a position difference at an interval of a predetermined first time period. The position difference is a difference between an actual tilt angle of the training rod and an instructed tilt angle of the training rod instructed by the training program. The determination unit obtains the position difference calculated by the position difference calculation unit every time when a predetermined second time period elapses. Further, the determination unit determines whether or not a position difference change amount generated in the second time period is the first threshold or lower. The motor drive unit drives the motor so that the position difference is accumulated and maintained if the determination unit determines that the position difference change amount generated in the second time period is the first threshold or lower. The position difference eliminating unit resets the accumulated and maintained position difference at a preset timing.

In this way, the determination unit obtains the position difference every time when the unit time (the second time period) elapses. In this way, the position difference change amount generated in the unit time (the second time period) can be calculated. In addition, the determination unit determines whether or not the position difference change amount generated in the unit time (the second time period) is the first threshold or lower. In this way, the determination unit can appropriately determine occurrence of the following status where the position difference is not zero but is not changed, or occurrence of the following status where the position difference is gradually changing.

Further, the position difference eliminating unit resets the accumulated and maintained position difference at a predetermined timing. In this way, when the position difference generated in the state where the position difference is not zero but is not changed, or the position difference generated in the state where the position difference gradually changes is increased, it is avoided that the determination unit determines an error. As a result, the patient can continue the training of a limb using this training apparatus.

The training rod may be capable of expanding and contracting in a longitudinal axis direction. Here, the longitudinal axis direction is a longitudinal direction of the training rod. Because the training rod is capable of expanding and contracting in a longitudinal axis direction, training of an upper limb or a lower limb can be carried out also in the longitudinal direction of the training rod.

The determination unit may determine an error if the position difference change amount generated in the second time period is higher than the first threshold. In this way, it is possible to appropriately determine that the limb cannot follow the training program by predicting a potential abnormality in this training apparatus and/or a potential obstacle that may affect continuation of the training.

The training apparatus may further include an information providing unit. The information providing unit provides visual or auditory information to a user including a patient, a training aid, and a health care worker, when the determination unit determines that an error has occurred.

In this way, the user can be informed of a status of the training apparatus and/or a potential obstacle that may affect continuation of the training.

The information providing unit may provide the information to the user when the patient has moved the training rod to reach a preset passing point in a training route set by the training program. In this way, the user can know that the training rod has been moved just in accordance with the training program. In addition, because the user is provided with the visual or auditory information when the patient has moved the training rod to reach the preset passing point, the patient can maintain motivation to continue the training.

When the determination unit determines that an error has occurred, rotation of the motor may be stopped. In this way, when an error has occurred, i.e., when it is determined that there is a potential obstacle that may affect continuation of the training, the training apparatus can be safely stopped.

The determination unit may further obtain the position difference every time when a predetermined third time period elapses. Further, the determination unit may determine whether or not the position difference change amount generated in the third time period is a second threshold or lower. Further, when the determination unit determines that the position difference change amount generated in the third time period is the second threshold or lower, the position difference eliminating unit may reset the accumulated and maintained position difference.

In this way, the accumulated and maintained position difference can be reset so that the patient can continue the training without always performing the motor control (position control) such that the actual tilt angle of the training rod follows the tilt angle instructed by the training program (instructed tilt angle).

The position difference eliminating unit may reset the accumulated and maintained position difference when the operation of the training rod is stopped. In this way, the position difference generated in the present training is not carried over to the next training and after, and hence the patient can continue the training.

The training apparatus may further include an instruction generation unit. The instruction generation unit generates a speed instruction including at least an acceleration instruction for accelerating the motor and a deceleration instruction for decelerating the motor in accordance with the training program. In this case, the motor drive unit may control the motor so as to follow only the speed instruction when the acceleration instruction is executed.

Because the speed instruction including at least the acceleration instruction and the deceleration instruction for driving the motor, the motor can be smoothly operated. As a result, the patient can operate the training rod as intended.

In addition, because the motor drive unit drives the motor so as to follow only the speed instruction when the acceleration instruction is executed, the motor can be controlled so that the position difference is accumulated and maintained. As a result, the patient can continue the training of the limb using the training apparatus even if the training rod is operated at a large tilt angle, for example, in which a relatively large motor torque is required, and a position difference is apt to occur. Further, because the position difference is accumulated and maintained, a state of the limb during the training can be monitored on the basis of the accumulated and maintained amount of the position difference.

The speed instruction may further include a constant speed instruction for rotating the motor at a constant speed disposed between the acceleration instruction and the deceleration instruction. In this case, the motor drive unit may control the motor so as to follow only the speed instruction when the constant speed instruction is executed.

Because the speed instruction further includes the constant speed instruction, even if the training rod is operated at a large tilt angle, the motor can be smoothly operated at a constant speed on the basis of feedback current from the motor. In addition, because the motor drive unit controls the motor so as to follow only the speed instruction when the constant speed instruction is executed, the motor can be controlled so that the position difference is accumulated and maintained. As a result, the patient can continue the training of the limb using the training apparatus even if the training rod is operated at a large tilt angle, for example, in which a relatively large motor torque is required, and a position difference is apt to occur. In addition, when the motor is rotated at a constant speed, it is possible to continue the training of the limb by a constant speed movement. Further, because the position difference is accumulated and maintained, a state of the limb of the patient during the training can be monitored on the basis of the accumulated and maintained amount of the position difference.

The instruction generation unit may further generate a position instruction for controlling the tilt angle of the training rod in accordance with the training program. In addition, the motor drive unit may control the motor so as to follow the speed instruction and the position instruction when the deceleration instruction is executed.

In this way, the motor drive unit can control the motor so that the training rod reaches a target tilt angle instructed by the training program with a difference as small as possible. As a result, when the position information of the training rod is fed back as visual information to the patient, for example, this position information can be appropriately used.

When the deceleration instruction is started, the position difference eliminating unit may reset the accumulated and maintained position difference. Here, the reset of the accumulated and maintained position difference means to set the accumulated and maintained position difference to zero. In this way, when the deceleration instruction is executed, it is possible to prevent the motor speed from being changed excessively by the position instruction.

Advantageous Effects

According to the present invention, it is possible to appropriately determine the following status where the position difference is not zero but is not changed, or the following status where the position difference gradually changes. In addition, it is possible to provide the training apparatus for rehabilitation support that controls the training rod so as to continue the training of the limb if it is determined that the training can be continued in the two following statuses as a result of the determination.

BRIEF DESCRIPTION OF DRAWINGS

FIG. 4 is a diagram illustrating an overall structure of the control unit.

DESCRIPTION OF EMBODIMENTS

1. First Embodiment (1) Overall Structure of Training Apparatus

Figure 1:
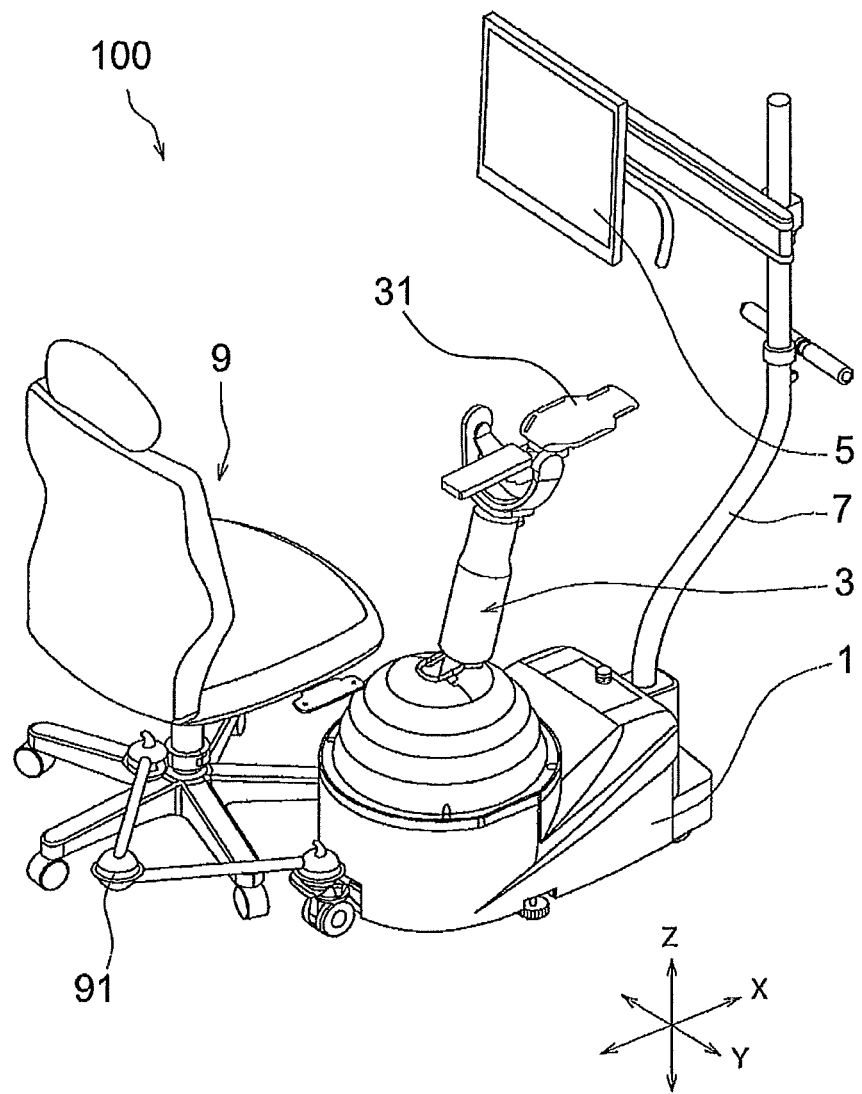
FIG. 1 is a diagram schematically illustrating a training apparatus.

An overall structure of a training apparatus 100 according to a first embodiment is described with reference to FIG. 1. FIG. 1 is a diagram schematically illustrating the training apparatus 100. The training apparatus 100 is a training apparatus for carrying out training aimed at motor function recovery of an upper limb and/or a lower limb of a user (a patient) in accordance with a predetermined training program.

Figure 2:
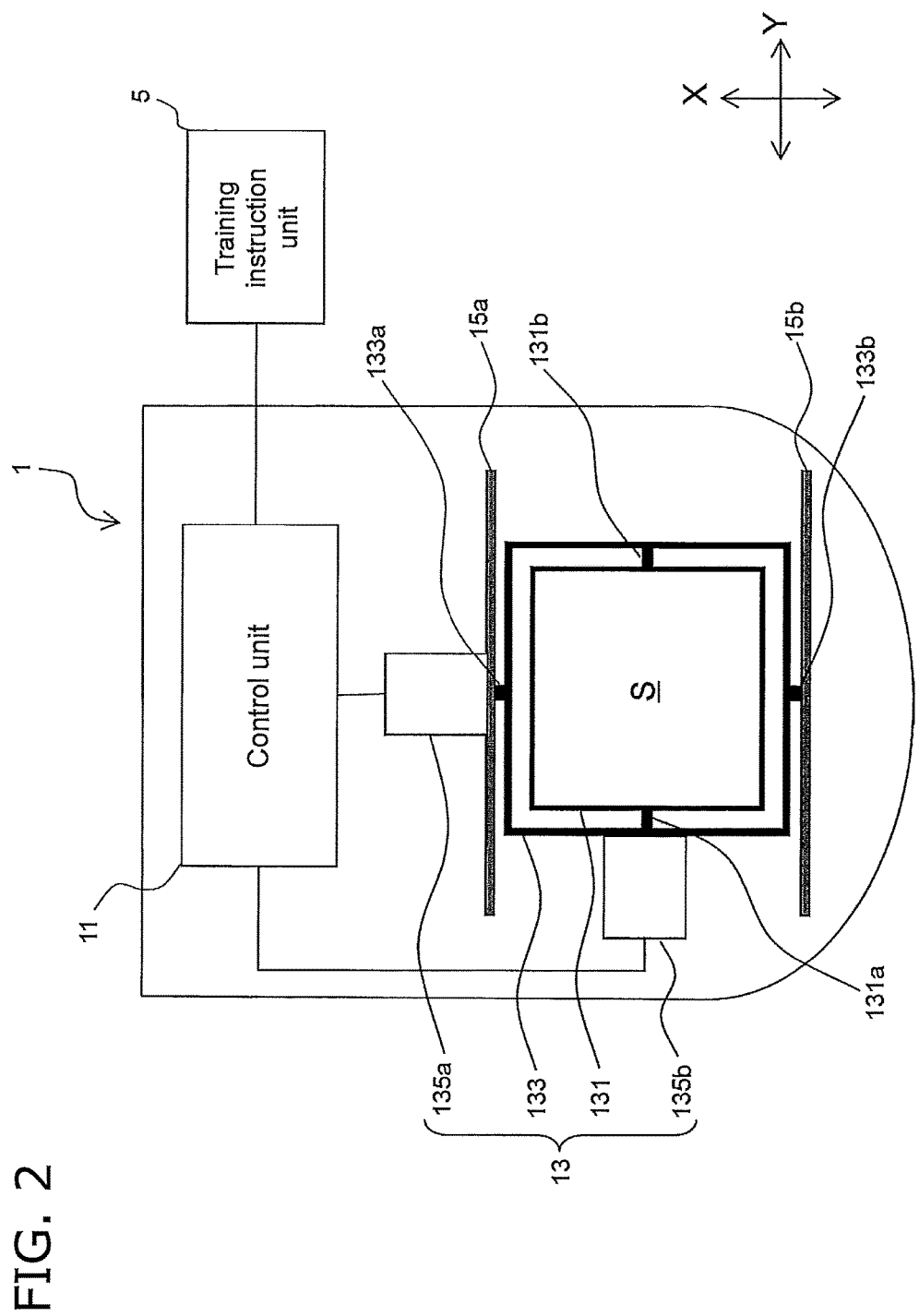
FIG. 2 is a diagram illustrating an overall structure of a control unit and a training rod tilt mechanism in a fixed frame.

The training apparatus 100 includes mainly a fixed frame 1, a training rod 3, and a training instruction unit 5. The fixed frame 1 is placed on or in the vicinity of a floor on which the training apparatus 100 is installed. In addition, the fixed frame 1 constitutes a main body casing of the training apparatus 100. The training rod 3 is attached to the fixed frame 1 via a training rod tilt mechanism 13 (FIG. 2) disposed inside the fixed frame 1. As a result, the training rod 3 can be tilted by the training rod tilt mechanism 13 in an X-axis direction parallel to a longitudinal direction of the fixed frame 1 and in a Y-axis direction parallel to a width direction of the fixed frame 1 (FIGS. 1 and 2).

Note that the training rod 3 may be capable of tilting only in the X-axis direction or the Y-axis direction, as necessary. In this case, the training rod 3 can tilt with one degree of freedom.

Figure 3:
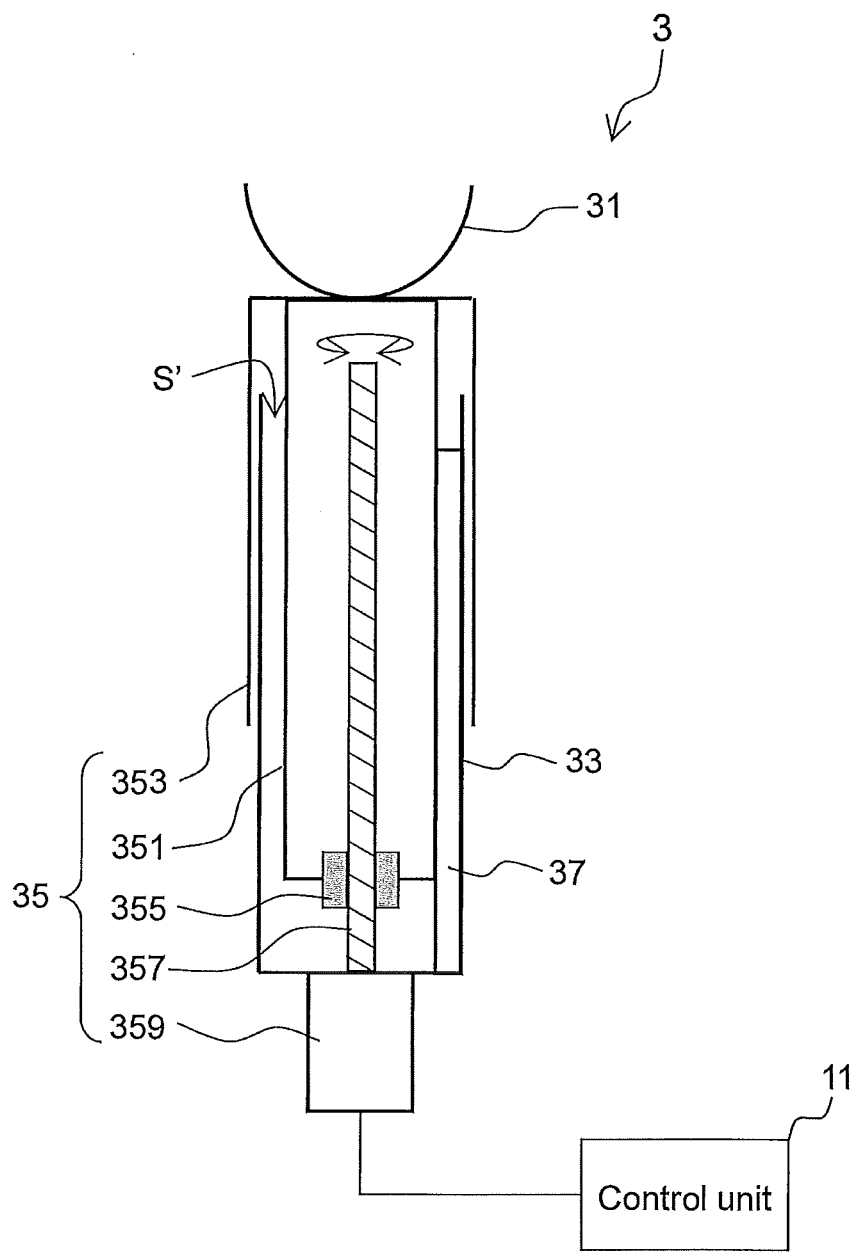
FIG. 3 is a diagram illustrating a structure of a training rod.

In addition, the training rod 3 may include inside an expansion/contraction mechanism in the longitudinal axis direction of the training rod 3 (FIG. 3). In this case, the training rod 3 can expand and contract in the longitudinal direction of the training rod 3, and hence can form a movement with at least 2 degrees of freedom or 3 degrees of freedom in cooperation with the training rod tilt mechanism 13.

In addition, the training rod 3 includes a limb support member 31 (described later) disposed on an upper end portion of the training rod 3. When the limb of the patient is supported by the limb support member 31, the training rod 3 can move the limb of the patient. Alternatively, the patient can move the training rod 3 by his/her intention.

The training instruction unit 5 is fixed to the fixed frame 1 via a fixing member 7. The training instruction unit 5 executes a preset training program and transmits a training rod operation instruction to a control unit 11 (FIG. 2), for operating the training rod 3, as necessary. In addition, the training instruction unit 5 provides a training route and an actual training movement of the limb of the patient as visual or auditory information by the preset training program. In this way, the patient can carry out the training of the limb while feeding back the training movement set by the training program and the actual movement.

Further, also when the limb of the patient tilted the training rod 3 to a target point (a target tilt angle) indicated by the training program, the training instruction unit 5 may inform the user with visual or auditory information that the training rod 3 has reached the target tilt angle. In this way, the patient can maintain motivation to continue the training.

In addition, when a determination unit 1134 described later (FIG. 7) determines that an error has occurred, the training instruction unit 5 provides the user with visual or auditory information. In this way, the user can be informed of a status of the training apparatus 100, and/or that there is a potential obstacle that may affect continuation of the training.

As the training instruction unit 5, an integrated computer system can be used, which includes a display device such as a liquid crystal display, a central processing unit (CPU), a storage device such as a random access memory (RAM), a read only memory (ROM), a hard disk and a solid state drive (SSD), and an input device such as a touch panel as necessary. In addition, the training instruction unit 5 may be constituted of a separate display device and other computer system. In this case, only the display device is fixed to the fixed frame 1 via the fixing member 7.

The training program executed by the training instruction unit 5 has five training modes, for example, including (i) guided mode, (ii) initiated mode, (iii) step initiated mode, (iv) follow assist mode, and (v) free mode. The guided mode is a training mode in which the training rod 3 moves the limb in a predetermined direction at a constant speed regardless of a movement of the limb of the patient. The initiated mode is a training mode in which a force that the patient intends to move the training rod 3 by the limb in a correct direction at an initial movement position with respect to the training route preset by the training program (also referred to as a force sensing trigger) is detected, and the training rod 3 moves the limb of the patient in a direction of the predetermined training route at a constant speed. The step initiated mode is a training mode in which the training rod 3 moves the limb of the patient by a constant distance in the training route when detecting the force sensing trigger at a predetermined point in the training route of the training rod 3. The follow assist mode is a training mode in which the force sensing trigger is detected every predetermined period, and a speed of the training rod 3 is changed in accordance with a level of the detected force sensing trigger. The free mode is a training mode in which the training rod 3 is moved so as to follow a movement of the limb of the patient.

In addition, the training apparatus 100 may further include a chair 9 for the patient to sit during the training. The chair 9 is connected to the fixed frame 1 via a chair connecting member 91, and hence stability of the training apparatus 100 can be secured. In addition, because the chair connecting member 91 is fixed with good reproductivity, the patient can carry out the training every time at the same position.

(2) Structure of Control Unit and Training Rod Tilt Mechanism

I. Overall Structure

Next, an overall structure of the control unit 11 and the training rod tilt mechanism 13 is described with reference to FIG. 2. FIG. 2 is a diagram illustrating an overall structure of the control unit 11 and the training rod tilt mechanism 13 disposed in the fixed frame 1.

The control unit 11 and the training rod tilt mechanism 13 are disposed in the fixed frame 1. The control unit 11 is connected to the training instruction unit 5 in a manner capable of transmitting and receiving signals. The control unit 11 receives the training rod operation instruction transmitted from the training instruction unit 5. In addition, the control unit 11 is electrically connected to an X-axis direction tilt motor 135*b* (described later), a Y-axis direction tilt motor 135*a* (described later), and an expansion/contraction motor 359 (FIG. 3). Accordingly, the control unit 11 drives the above-mentioned three motors on the basis of the training rod operation instruction. Note that structure and operation of the control unit 11 will be described later in detail.

The training rod tilt mechanism 13 is attached to the fixed frame 1 in a manner capable of tilting via training rod tilt mechanism fixing members 15*a* and 15*b* fixed to the fixed frame 1. For this reason, the training rod tilt mechanism 13 can tilt the training rod 3 in the X-axis direction and in the Y-axis direction (with 2 degrees of freedom). Hereinafter, a structure of the training rod tilt mechanism 13 is described in detail.

Note that the training rod tilt mechanism 13 may be configured to tilt the training rod 3 only in the X-axis direction or in the Y-axis direction (with one degree of freedom). Alternatively, the training rod tilt mechanism 13 may be selectable whether to tilt the training rod 3 with one degree of freedom or with 2 degrees of freedom.

II. Structure of Training Rod Tilt Mechanism

The structure of the training rod tilt mechanism 13 of this embodiment is described with reference to FIG. 2. The training rod tilt mechanism 13 enables to tilt the training rod 3 in the X-axis direction and in the Y-axis direction by a "gimbal" mechanism that enables to move two axes. Here, the X-axis direction is a horizontal direction parallel to the longitudinal direction of the fixed frame 1 in FIG. 2. The Y-axis direction is a horizontal direction parallel to the width direction of the fixed frame 1 in FIG. 2.

The training rod tilt mechanism 13 includes an X-axis direction tilt member 131 and a Y-axis direction tilt member 133 (described later), as well as the X-axis direction tilt motor 135b and the Y-axis direction tilt motor 135a respectively corresponding to the tilt members.

Further, when the training rod tilt mechanism 13 tilts the training rod 3 with one degree of freedom, it is sufficient that the training rod tilt mechanism 13 includes only the X-axis direction tilt member 131 and the X-axis direction tilt motor 135b, or the Y-axis direction tilt member 133 and the Y-axis direction tilt motor 135a. Alternatively, even if the training rod tilt mechanism 13 includes the above-mentioned two members and two motors, the training rod tilt mechanism 13 can tilt the training rod 3 with one degree of freedom by disabling one combination of the member and the motor.

The X-axis direction tilt member 131 is disposed inside a space of the Y-axis direction tilt member 133. In addition, the X-axis direction tilt member 131 includes two shafts 131a and 131b extending outward from two side surfaces having normals parallel to the Y-axis. The two shafts 131a and 131b are supported respectively by the two side surfaces having normals parallel to the Y-axis of the Y-axis direction tilt member 133 in a manner capable of rotating the X-axis direction tilt member 131 about the Y-axis. In this way, the X-axis direction tilt member 131 can change an angle between the training rod 3 fixed to the X-axis direction tilt member 131 and the X-axis. Here, changing the angle between the training rod 3 and the X-axis may be referred to as "tilting in the X-axis direction".

Note that the training rod 3 is fixed to the X-axis direction tilt member 131 in a state where a part of the training rod 3 is inserted in a space S of the X-axis direction tilt member 131.

In the same manner, the Y-axis direction tilt member 133 includes two shafts 133a and 133b extending outward from two side surfaces having normals parallel to the X-axis. The two shafts 133a and 133b are supported respectively by the training rod tilt mechanism fixing members 15a and 15b in a manner capable of rotating the Y-axis direction tilt member 133 about the X-axis. In this way, the Y-axis direction tilt member 133 can rotate about the X-axis with respect to the training rod tilt mechanism fixing members 15a and 15b. As a result, the Y-axis direction tilt member 133 can change an angle between the training rod 3 fixed to the X-axis direction tilt member 131 and the Y-axis. Here, changing the angle between the training rod 3 and the Y-axis may be referred to as "tilting in the Y-axis direction".

In this way, the Y-axis direction tilt member 133 tilts the training rod 3 in the Y-axis direction, and the X-axis direction tilt member 131 tilts the training rod 3 in the X-axis direction. Accordingly, the training rod tilt mechanism 13 can tilt the training rod 3 with two-dimensional degrees of freedom. Further, although the X-axis direction tilt member 131 is disposed inside the space of the Y-axis direction tilt member 133 in FIG. 2, it is possible to modify the design so that the X-axis direction tilt member 131 is disposed outside the space of the Y-axis direction tilt member 133 so as to tilt the corresponding member.

The Y-axis direction tilt motor 135a is fixed to the training rod tilt mechanism fixing member 15a. In addition, an output rotation shaft of the Y-axis direction tilt motor 135a is connected, via a speed reduction mechanism (not shown), to the shaft 133a extending from the Y-axis direction tilt member 133 so as to rotate the shaft 133a. Accordingly, the Y-axis direction tilt motor 135a rotates the Y-axis direction tilt member 133 about the X-axis. Further, the Y-axis direction tilt motor 135a is electrically connected to the control unit 11. Accordingly, the Y-axis direction tilt motor 135a can tilt the training rod 3 in the Y-axis direction by control by the control unit 11.

The X-axis direction tilt motor 135b is fixed to the surface that pivotally supports a shaft 131a extending from the X-axis direction tilt member 131, among four side surfaces of the Y-axis direction tilt member 133. In addition, an output rotation shaft of the X-axis direction tilt motor 135b is connected to the shaft 131a extending from the X-axis direction tilt member 131 via a speed reduction mechanism (not shown) so as to rotate the shaft 131a. Accordingly, the X-axis direction tilt motor 135b can rotate the X-axis direction tilt member 131 about the Y-axis. Further, the X-axis direction tilt motor 135b is electrically connected to the control unit 11. Accordingly, the X-axis direction tilt motor 135b can tilt the training rod 3 in the X-axis direction by control by the control unit 11.

In this way, the Y-axis direction tilt motor 135a and the X-axis direction tilt motor 135b tilt the training rod 3 respectively in the X-axis direction and in the Y-axis direction with one degree of freedom by control by the control unit 11. In other words, because the X-axis direction tilt motor 135b and the Y-axis direction tilt motor 135a are provided, the training rod 3 can be controlled in a two-dimensional manner.

As the Y-axis direction tilt motor 135a and the X-axis direction tilt motor 135b, an electric motor such as a servo motor or a brush-less motor can be used, for example.

(3) Structure of Training Rod

I. Overall Structure

Next, a structure of the training rod 3 is described with reference to FIG. 3. First, an overall structure of the training rod 3 is described. FIG. 3 is a diagram illustrating a structure of the training rod 3. The training rod 3 includes the limb support member 31, a fixed stay 33, and an expansion/contraction mechanism 35. The limb support member 31 is fixed to an upper end portion of a cover 353 (described later) of the expansion/contraction mechanism 35. The limb support member 31 is a member supporting the limb of the patient. The fixed stay 33 constitutes a main body of the training rod 3. In addition, the fixed stay 33 has a space S' for housing a movable stay 351 (described later) of the expansion/contraction mechanism 35. Further, the fixed stay 33 includes a fixing member (not shown) for fixing the training rod 3 to the X-axis direction tilt member 131 of the training rod tilt mechanism 13. When the fixed stay 33 is fixed to the X-axis direction tilt member 131 with the fixing member of the fixed stay 33, the training rod 3 is fixed to the training rod tilt mechanism 13.

The expansion/contraction mechanism 35 is provided to the fixed stay 33 in a movable manner along the longitudinal direction of the fixed stay 33. In this way, the training rod 3 can expand and contract in the longitudinal direction of the training rod 3. Hereinafter, a structure of the expansion/contraction mechanism 35 is described in detail.

II. Structure of Expansion/Contraction Mechanism

As illustrated in FIG. 3, the expansion/contraction mechanism 35 includes the movable stay 351, the cover 353, a nut 355, a threaded shaft 357, and the expansion/contraction motor 359.

The movable stay 351 is inserted in the space S' formed in the fixed stay 33. In addition, the movable stay 351 includes a slide unit (not shown). This slide unit is slidably engaged with a guide rail 37 provided on an inner wall of the fixed stay 33. As a result, the movable stay 351 can move along the guide rail 37 in the space S' formed in the fixed stay 33. The cover 353 is fixed to the upper end portion of the movable stay 351. In this way, the cover 353 can move in accordance with movement of the movable stay 351. In addition, the cover 353 includes the limb support member 31 on the upper end portion. Accordingly, the cover 353 can move the limb support member 31 in the extending direction of the fixed stay 33.

The nut 355 is attached to a bottom portion of the movable stay 351. The nut 355 is engaged with the threaded shaft 357 (described later). The threaded shaft 357 is a thread member elongated in parallel to the longitudinal direction of the fixed stay 33. In addition, the threaded shaft 357 is engaged with the nut 355. Accordingly, when the threaded shaft 357 rotates, the nut 355 moves along the longitudinal direction of the threaded shaft 357 (namely, the longitudinal direction of the fixed stay 33 (the longitudinal axis direction)).

As described above, because the nut 355 is fixed to the bottom portion of the movable stay 351, when the nut 355 moves along the extending direction of the threaded shaft 357, the movable stay 351 can move along the longitudinal direction of the fixed stay 33.

The expansion/contraction motor 359 is fixed to a bottom portion of the fixed stay 33. In addition, an output rotation shaft of the expansion/contraction motor 359 is connected to an end portion in the longitudinal direction of the threaded shaft 357 so as to rotate the threaded shaft 357 about the axis. Further, the expansion/contraction motor 359 is electrically connected to the control unit 11. Accordingly, the expansion/contraction motor 359 can rotate the threaded shaft 357 about the axis of the threaded shaft 357 by control by the control unit 11.

As described above, the nut 355 is engaged with the threaded shaft 357, and hence the nut 355 can move along the longitudinal direction of the threaded shaft 357 in accordance with rotation of the threaded shaft 357. Accordingly, the movable stay 351 can move along the longitudinal direction of the fixed stay 33 (longitudinal axis direction) in accordance with rotation of the expansion/contraction motor 359.

(4) Structure of Control Unit

I. Overall Structure

Next, an overall structure of the control unit 11 is described with reference to FIG. 4. FIG. 4 is a diagram illustrating an overall structure of the control unit 11. As the control unit 11, it is possible to use a microcomputer system, for example, which includes a CPU, a storage device such as a RAM, a ROM, a hard disk drive, and an SSD, an interface for converting an electric signal, and the like. In addition, a part or a whole of functions of the control unit 11 described below may be realized by a program that can be executed by the microcomputer system. In addition, the program may be stored in the storage device of the microcomputer system. Further, a part or a whole of functions of the control unit 11 may be realized by a custom IC or the like.

The control unit 11 includes an instruction generation unit 111, and motor control units 113a, 113b, and 113c.

The instruction generation unit 111 is connected to the training instruction unit 5 and the motor control units 113a, 113b, and 113c in a manner capable of transmitting and receiving signals. The instruction generation unit 111 generates instructions for the motor control units 113a, 113b, and 113c to respectively drive the Y-axis direction tilt motor 135a, the X-axis direction tilt motor 135b, and the expansion/contraction motor 359 on the basis of the training rod operation instruction transmitted from the training instruction unit 5.

The instructions generated by the instruction generation unit 111 include a speed instruction and a position instruction. The speed instruction is an instruction for controlling rotation speed of the motor (an amount of change of the tilt angle or the expansion/contraction length of the training rod 3 per unit time). In addition, the position instruction is an instruction for controlling the tilt angle or the expansion/contraction length of the training rod 3.

As described later, when each of the motor control units 113a, 113b, and 113c controls each of the motors on the basis of the speed instruction, the motor is controlled to follow the speed instructed by the speed instruction. In other words, if there is a difference (speed difference) between the speed instructed by the speed instruction and the actual rotation speed of the motor, each of the motor control units 113a, 113b, and 113c controls the motor so as to eliminate the speed difference.

On the other hand, when each of the motor control units 113a, 113b, and 113c controls the motor on the basis of the position instruction, the motor is controlled to allow the tilt angle or the expansion/contraction length of the training rod 3 to follow the tilt angle instructed by the position instruction (instructed tilt angle) or the expansion/contraction length instructed by the position instruction (instructed expansion/contraction length). In other words, if there is a difference (position difference) between the tilt angle instructed by the position instruction and the actual tilt angle of the training rod 3, or between the expansion/contraction length instructed by the position instruction and the actual expansion/contraction length of the training rod 3, each of the motor control units 113a, 113b, and 113c controls the motor so as to eliminate the position difference.

Note that the speed instruction and the position instruction generated by the instruction generation unit 111 are functions of time. On the other hand, the training rod operation instruction transmitted from the training instruction unit 5 includes at least information of the tilt angle to which the training rod 3 is moved (target position information) and information of the amount of change of the tilt angle or the expansion/contraction length of the training rod 3 per unit time (the tilt angle speed or the expansion/contraction length speed) (target speed information), and further includes information of an acceleration rate for the tilt angle speed of the training rod 3 or the expansion/contraction length speed to reach a desired tilt angle speed or expansion/contraction length speed (acceleration rate information) and information of a deceleration rate for stopping the moving training rod 3 (deceleration rate information).

In other words, the training rod operation instruction as a base for generating the speed instruction and the position instruction does not include information of time. However, the training rod operation instruction includes information of distance (corresponding to the target position information) and information of speed (corresponding to the target speed information), and further includes information of acceleration rate (corresponding to the acceleration rate information and the deceleration rate information). Accordingly, the information of time can be derived from these information.

Thus, the instruction generation unit 111 can generate the speed instruction and the position instruction as functions of time, by calculating with appropriate combination of the target position information and the target speed information, as well as the acceleration rate information and the deceleration rate information, included in the training rod operation instruction.

Figure 5A:
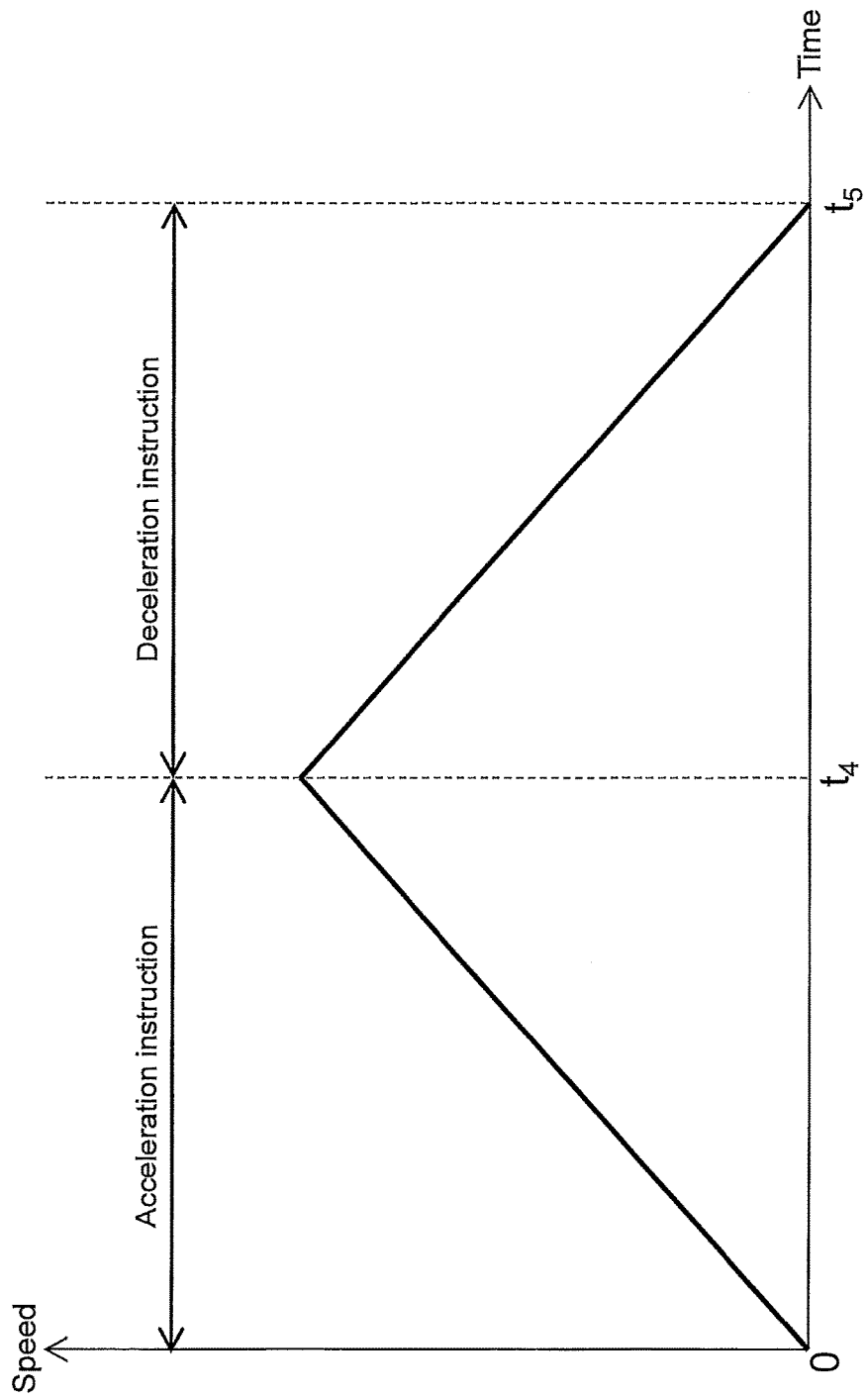
FIG. 5A is a graph illustrating a triangular speed locus type speed instruction.
Figure 5B:
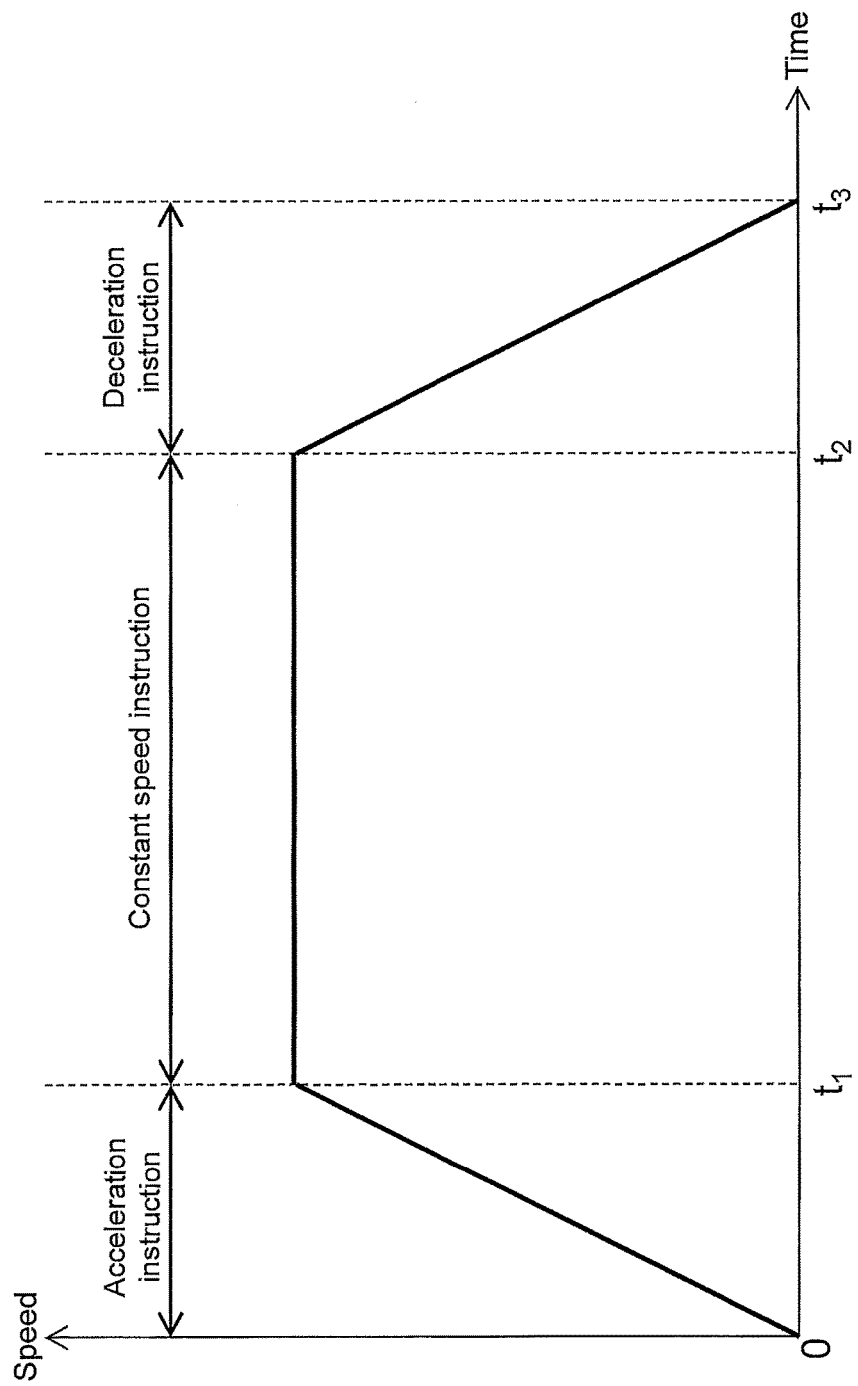
FIG. 5B is a graph illustrating a trapezoidal speed locus type speed instruction.

In addition, the speed instructions generated by the instruction generation unit 111 include two types of speed instructions as illustrated in FIGS. 5A and 5B. One of them is the speed instruction as illustrated in FIG. 5A, which includes only an acceleration instruction for accelerating the motor at a constant acceleration rate and a deceleration instruction for decelerating the motor at a constant deceleration rate. This speed instruction can be expressed as a graph having a triangular shape in a coordinate system in which the horizontal axis represents time, while the vertical axis represents speed. Accordingly, this speed instruction may be referred to as a triangular speed locus type speed instruction. The case where the speed instruction becomes the triangular speed locus type is, for example, a case where a moving distance of the training rod 3 is short when moving from a current tilt angle of the training rod 3 to a target tilt angle of the training rod 3 instructed by the training instruction unit 5, a case where the acceleration rate or the deceleration rate of the motor instructed by the training rod operation instruction is small, or the like.

In this way, because the speed instruction includes the acceleration instruction and the deceleration instruction, the motor control units 113a, 113b, and 113c can smoothly control the motors.

The other type is the speed instruction as illustrated in FIG. 5B, which includes, in addition to the acceleration instruction and the deceleration instruction, a constant speed instruction for rotating the motor at a constant speed. This speed instruction can be expressed as a graph having a trapezoidal shape in a coordinate system in which the horizontal axis represents time, while the vertical axis represents speed. Accordingly, this speed instruction may be referred to as a trapezoidal speed locus type speed instruction. The case where the speed instruction becomes the trapezoidal speed locus is, for example, a case where a moving distance of the training rod 3 is long when moving from a current tilt angle of the training rod 3 to a target tilt angle of the training rod 3 instructed by the training instruction unit 5, a case where the acceleration rate or the deceleration rate of the motor is large, or the like.

In this way, because the speed instruction further includes the constant speed instruction, the motor control units 113a, 113b, and 113c can smoothly control the motors even if the training rod 3 moves at a large tilt angle.

Figure 6:
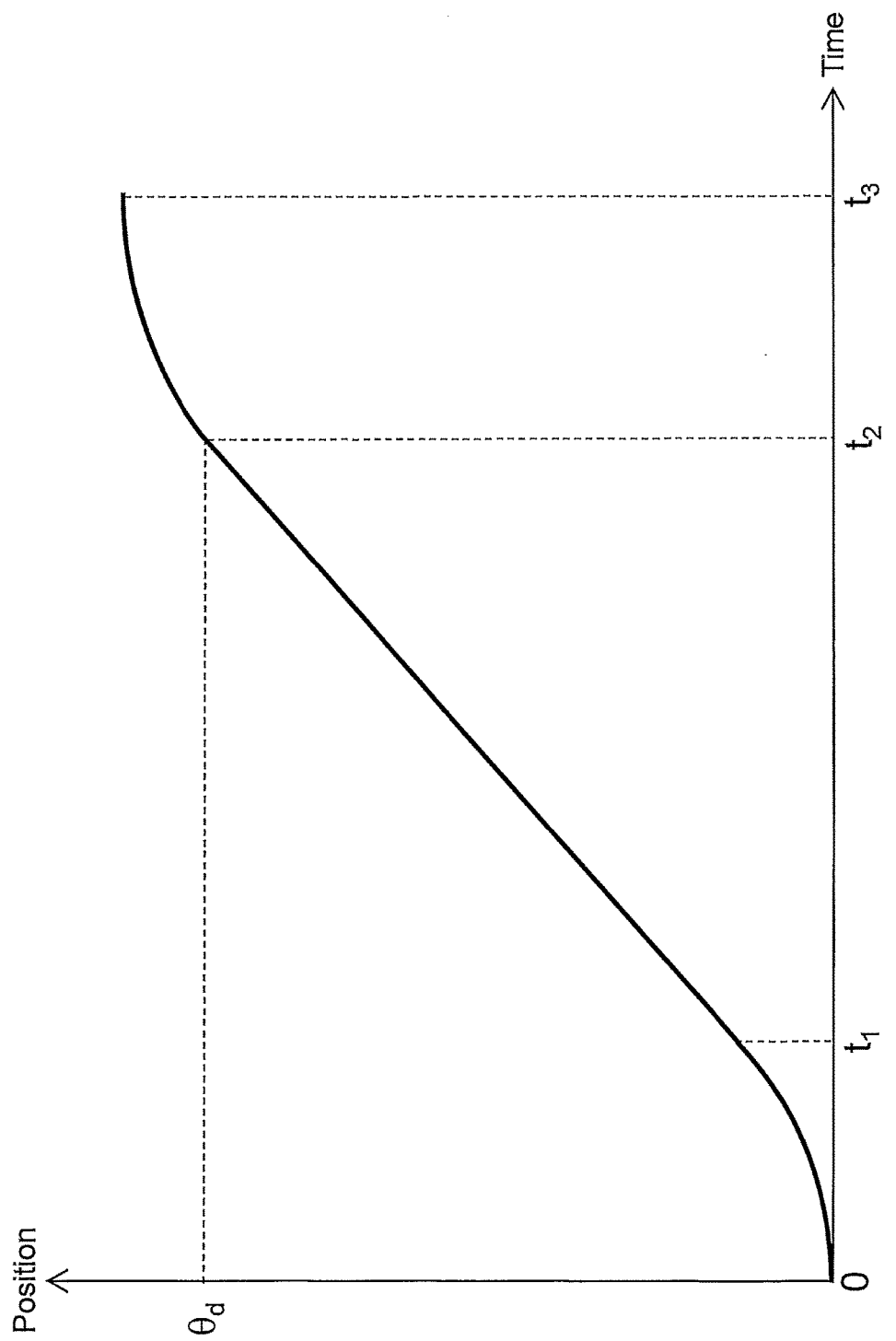
FIG. 6 is a graph illustrating a position instruction.

On the other hand, the position instruction generated by the instruction generation unit 111 has a shape as illustrated in FIG. 6 in a coordinate system in which the horizontal axis represents time, while the vertical axis represents position (tilt angle). The position instruction corresponds to an integrated value of the speed instruction over time. The position instruction illustrated in FIG. 6 is a position instruction corresponding to the trapezoidal speed locus type speed instruction illustrated in FIG. 5B. Accordingly, in the trapezoidal speed locus type speed instruction, the position instruction has a downward-convex parabola shape with a vertex at time point 0 in a period between time points 0 to $t_1$ (during an acceleration instruction interval) while the speed increases with a positive gradient. In a period between time points $t_1$ and $t_2$ (a constant speed instruction interval) until the speed becomes a line parallel to a horizontal axis in the speed instruction, the position instruction increases linearly with a positive gradient. Further, in a period between time points $t_2$ and $t_3$ (during a deceleration instruction interval) while the speed decreases with a negative gradient in the speed instruction, the position instruction has an upward-convex parabola shape with a vertex at time point $t_3$.

The motor control units 113a, 113b, and 113c are connected to the instruction generation unit 111 in a manner capable of transmitting and receiving signals. Accordingly, the motor control units 113a, 113b, and 113c can receive the speed instruction and the position instruction from the instruction generation unit 111. In addition, the motor control units 113a, 113b, and 113c are electrically connected to the Y-axis direction tilt motor 135a, the X-axis direction tilt motor 135b, and the expansion/contraction motor 359, respectively. Accordingly, the motor control units 113a, 113b, and 113c can control the motors in accordance with the speed instruction and/or the position instruction.

Further, the motor control units 113a, 113b, and 113c are connected to a first rotation information detection sensor 135a-1 for the Y-axis direction tilt motor 135a, a second rotation information detection sensor 135b-1 for the X-axis direction tilt motor 135b, and a third rotation information detection sensor 359-1 for the expansion/contraction motor 359, respectively, in a manner capable of transmitting and receiving signals.

The first rotation information detection sensor 135a-1, the second rotation information detection sensor 135b-1, and the third rotation information detection sensor 359-1 are fixed to the output rotation shaft of the Y-axis direction tilt motor 135a, the output rotation shaft of the X-axis direction tilt motor 135b, and the output rotation shaft of the expansion/contraction motor 359, respectively. In this way, the first rotation information detection sensor 135a-1, the second rotation information detection sensor 135b-1, and the third rotation information detection sensor 359-1 can output an amount of rotation of the Y-axis direction tilt motor 135a, an amount of rotation of the X-axis direction tilt motor 135b, and an amount of rotation of the expansion/contraction motor 359, respectively.

As the first rotation information detection sensor 135a-1, the second rotation information detection sensor 135b-1, and the third rotation information detection sensor 359-1, it is possible to use sensors that can measure an amount of rotation of the output rotation shaft of the motor. As such the sensor, for example, an encoder such as an incremental type encoder or an absolute type encoder can be appropriately used. When encoders are used as the sensors, the first rotation information detection sensor 135a-1, the second rotation information detection sensor 135b-1, and the third rotation information detection sensor 359-1 output pulse signals corresponding to amounts of rotation of the Y-axis direction tilt motor 135a, an amount of rotation of the X-axis direction tilt motor 135b, and an amount of rotation of the expansion/contraction motor 359, respectively.

In this way, because the motor control units 113a, 113b, and 113c are connected to the first rotation information detection sensor 135a-1, the second rotation information detection sensor 135b-1, and the third rotation information detection sensor 359-1, respectively, for measuring amounts of rotation of the output rotation shafts of the motors, the motor control units 113a, 113b, and 113c can control the motors in consideration of actual amounts of rotation of the motors.

Next, the motor control units 113a, 113b, and 113c are described in detail. In the following description, the motor control unit 113a is exemplified and described. It is because other motor control units 113b and 113c have the same structure and the same operation as the motor control unit 113a.

II. Structure of Motor Control Unit

Figure 7:
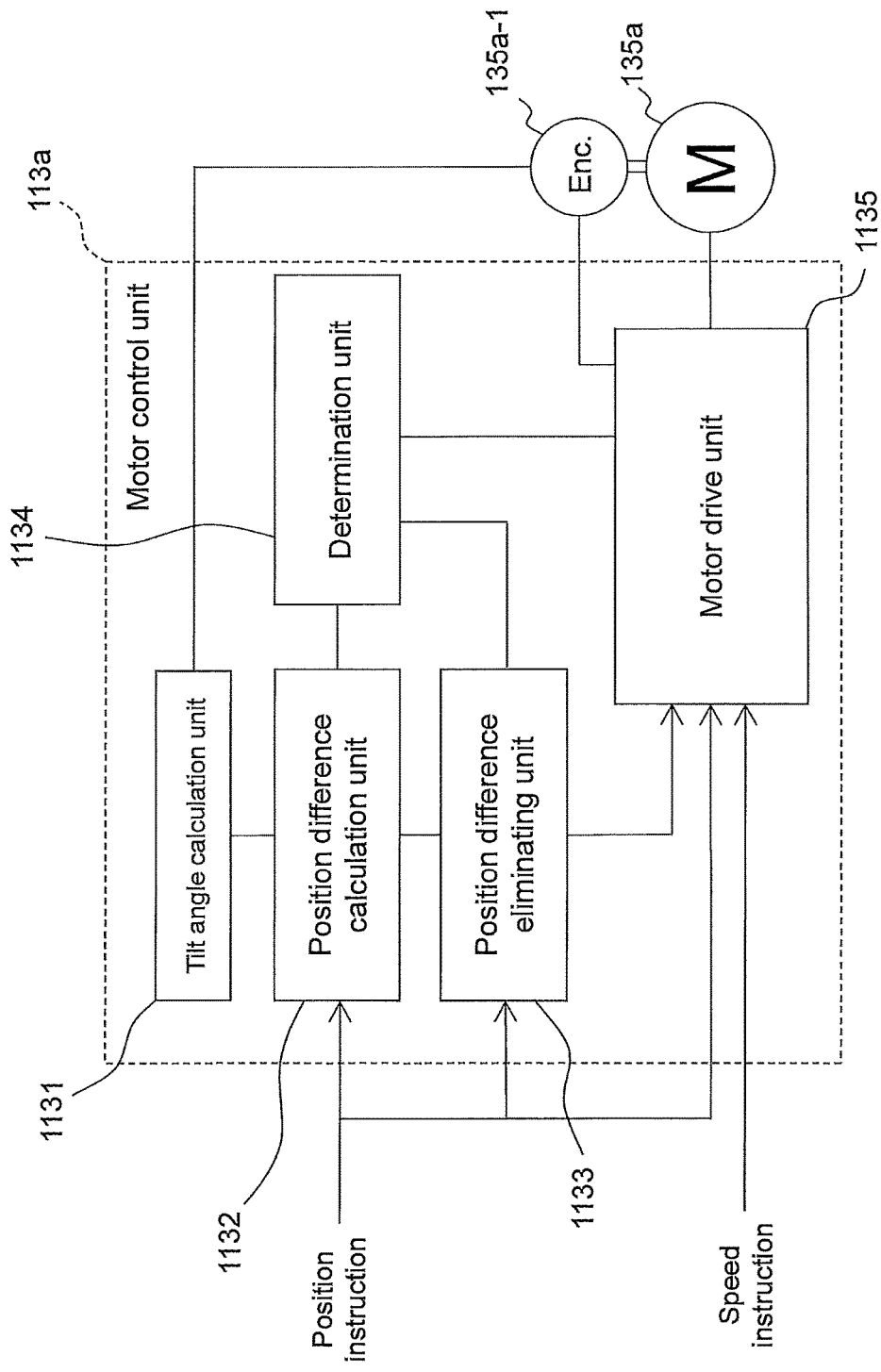
FIG. 7 is a diagram illustrating a structure of a motor control unit.

A structure of the motor control unit 113a is described with reference to FIG. 7. FIG. 7 is a diagram illustrating a structure of the motor control unit 113a.

The motor control unit 113a includes a tilt angle calculation unit 1131, a position difference calculation unit 1132, a position difference eliminating unit 1133, the determination unit 1134, and a motor drive unit 1135.

The tilt angle calculation unit 1131 is connected to the first rotation information detection sensor 135a-1 in a manner capable of transmitting and receiving signals. In this way, the pulse signal output corresponding to the amount of rotation of the output rotation shaft of the Y-axis direction tilt motor 135a measured by the first rotation information detection sensor 135a-1 can be input to the tilt angle calculation unit 1131. Further, the tilt angle calculation unit 1131 calculates a tilt angle of the training rod 3 (in the Y-axis direction) on the basis of the number of pulses included in the pulse signal output from the first rotation information detection sensor 135a-1.

The position difference calculation unit 1132 is connected to the tilt angle calculation unit 1131 in a manner capable of transmitting and receiving signals. In this way, the tilt angle of the training rod 3 calculated by the tilt angle calculation unit 1131 is input to the position difference calculation unit 1132. In addition, the position difference calculation unit 1132 is connected to the instruction generation unit 111 in a manner capable of transmitting and receiving signals. In this way, the position instruction generated by the instruction generation unit 111 is input to the position difference calculation unit 1132.

The position difference calculation unit 1132 calculates a difference between the actual tilt angle of the training rod 3 calculated by the tilt angle calculation unit 1131 and the tilt angle of the training rod 3 instructed by the position instruction (instructed tilt angle), as the position difference, at an interval of a first time period $T_1$. The first time period $T_1$ as the interval for calculating the position difference corresponds to a control interval for the motor drive unit 1135 to control the Y-axis direction tilt motor 135a.

The position difference eliminating unit 1133 is connected to the position difference calculation unit 1132 in a manner capable of transmitting and receiving signals. In this way, the position difference is input to the position difference eliminating unit 1133 from the position difference calculation unit 1132. In addition, the position difference eliminating unit 1133 is connected to the determination unit 1134 in a manner capable of transmitting and receiving signals. In this way, on the basis of a signal from the determination unit 1134, the position difference eliminating unit 1133 can switch whether or not to perform correction of the position difference. Further, the position difference eliminating unit 1133 is connected to the instruction generation unit 111 in a manner capable of transmitting and receiving signals. In this way, the position difference eliminating unit 1133 can receive the position instruction from the instruction generation unit 111.

In addition, the position difference eliminating unit 1133 is connected to a position control unit 1135-2 (FIG. 8) of the motor drive unit 1135 in a manner capable of transmitting and receiving signals, as described later. In this way, the position difference eliminating unit 1133 can output the corrected position difference (reset position difference) to the position control unit 1135-2.

At a preset timing, the position difference eliminating unit 1133 resets the accumulated and maintained position difference output from the position difference calculation unit 1132. In this embodiment, a timing for resetting the position difference is set to (i) a timing when the determination unit 1134 determines that the position difference change amount generated in a third time period $T_3$ (described later) is a second threshold $\phi_2$ (described later) or lower, (ii) a timing when operation of the training rod 3 (the Y-axis direction tilt motor 135a) is stopped, and/or, (iii) a timing when the tilt angle of the training rod 3 has reached a deceleration start position (described later). The position difference eliminating unit 1133 may reset the accumulated and maintained position difference at all the three timings, or may reset the accumulated and maintained position difference at one or two of the three timings.

Further, if any one of the timings (i) to (iii) is not applicable, the position difference eliminating unit 1133 does not reset the accumulated and maintained position difference but output the position difference output from the position difference calculation unit 1132, as it is.

Among the three timings described above, the timing (i) can be detected on the basis of a signal from the determination unit 1134. On the other hand, the timings (ii) and (iii) are detected when the position difference eliminating unit 1133 detects the actual tilt angle of the training rod 3. The position difference eliminating unit 1133 can detect the actual tilt angle of the training rod 3 by subtracting the position difference from the instructed tilt angle instructed by the position instruction. However, without limiting to this, the position difference eliminating unit 1133 may obtain the actual tilt angle of the training rod 3 directly from the tilt angle calculation unit 1131.

In addition, the position difference eliminating unit 1133 resets the accumulated and maintained position difference by the following two methods.

A first method includes temporarily connecting the position control unit 1135-2 of the motor drive unit 1135 (FIG. 8) to the combining unit (described later) at the timing described above, and temporarily controlling the Y-axis direction tilt motor 135a so that the tilt angle of the training rod 3 follows the instructed tilt angle (the position control). In this way, the actual tilt angle of the training rod 3 matches the instructed tilt angle. As a result, the position difference is prevented from being excessively accumulated and maintained.

Further, the matching between the actual tilt angle of the training rod 3 and the instructed tilt angle as a result of the control so that the tilt angle of the training rod 3 follows the instructed tilt angle (the position control) may be referred to as "physical matching between the actual tilt angle of the training rod 3 and the instructed tilt angle", or "physical reset of the position difference".

A second method includes setting the position difference value as a parameter handled by the control unit 11 to zero at the timing described above. In this method of resetting the position difference, even if the position difference is reset, the position difference between the actual tilt angle of the training rod 3 and the instructed tilt angle is maintained. In this way, by setting the position difference value as a parameter to zero, a level of the accumulated and maintained position difference (described later) is prevented from being increased, and it is avoided to determine an error. In addition, as described later, the position control unit 1135-2 is controlled on the basis of the corrected position difference output from the position difference eliminating unit 1133. In this way, when the position difference as the parameter is set to zero, a second control amount (described later) output from the position control unit 1135-2 can be decreased. As a result, it is possible to prevent a rotation speed of the Y-axis direction tilt motor 135a from being excessively increased on the basis of an increase of the position difference. Accordingly, the training can be safely continued.

The determination unit 1134 is connected to the position difference calculation unit 1132 in a manner capable of transmitting and receiving signals. Accordingly, the determination unit 1134 can receive the position difference from the position difference calculation unit 1132. In addition, the determination unit 1134 is connected to the position difference eliminating unit 1133 and the motor drive unit 1135 (described later) in a manner capable of transmitting and receiving signals. Accordingly, the determination unit 1134 can determine an operation of the position difference eliminating unit 1133 and the motor drive unit 1135 on the basis of whether or not the following first condition and/or second condition are "true" or "false".

The determination unit 1134 obtains the position difference output from the position difference calculation unit 1132, every time when a second time period $T_2$ elapses. As described later, because the position difference is obtained every time when the preset second time period $T_2$ elapses, the position difference change amount per unit time can be calculated. As a result, the determination unit 1134 can appropriately determine a case where a following status in which the position difference is not zero but is not changed has occurred, or a case where a following status in which the position difference gradually changes has occurred.

Further, the determination unit 1134 determines whether or not the position difference change amount generated in the second time period $T_2$ is a first threshold $\phi_1$ or lower (first condition). Further, if the first condition is "true", the determination unit 1134 instructs the motor drive unit 1135 to drive the Y-axis direction tilt motor 135a so that the position difference is accumulated and maintained.

On the other hand, if the determination unit 1134 determines that the first condition is "false", an error is determined. If it is determined that the first condition is "false", the determination unit 1134 instructs the motor control unit 113a to perform an error process. If the first condition is "false", it means that the position difference has rapidly changed, and further, it indicates that the limb of the patient cannot follow the set training program, which may affect continuation of the training.

For this reason, if the first condition is "false", the error process is performed, and the training apparatus 100 can be safely operated or stopped. As a result, the training can be safely continued or finished.

In addition, the determination unit 1134 obtains the position difference output from the position difference calculation unit 1132 every time when the third time period $T_3$ elapses. Further, the determination unit 1134 determines whether or not the position difference change amount generated in the third time period $T_3$ is the second threshold $\phi_2$ or lower (the second condition). Further, if the second condition is "true", the determination unit 1134 instructs the position difference eliminating unit 1133 to reset the position difference.

In this way, if the position difference change amount generated in the third time period $T_3$ is the second threshold $\phi_2$ or lower, the position difference eliminating unit 1133 can reset the position difference.

The motor drive unit 1135 is connected to the instruction generation unit 111 in a manner capable of transmitting and receiving signals. In this way, the position instruction and the speed instruction are input to the motor drive unit 1135 from the instruction generation unit 111. In addition, the motor drive unit 1135 is electrically connected to the Y-axis direction tilt motor 135a. Further, the motor drive unit 1135 is connected to the first rotation information detection sensor 135a-1 in a manner capable of transmitting and receiving signals.

In this way, the motor drive unit 1135 can control the Y-axis direction tilt motor 135a on the basis of the speed instruction and/or the position instruction, and the amount of rotation of the Y-axis direction tilt motor 135a. Details of the motor drive unit 1135 will be described later.

III. Structure of Motor Drive Unit

Figure 8:
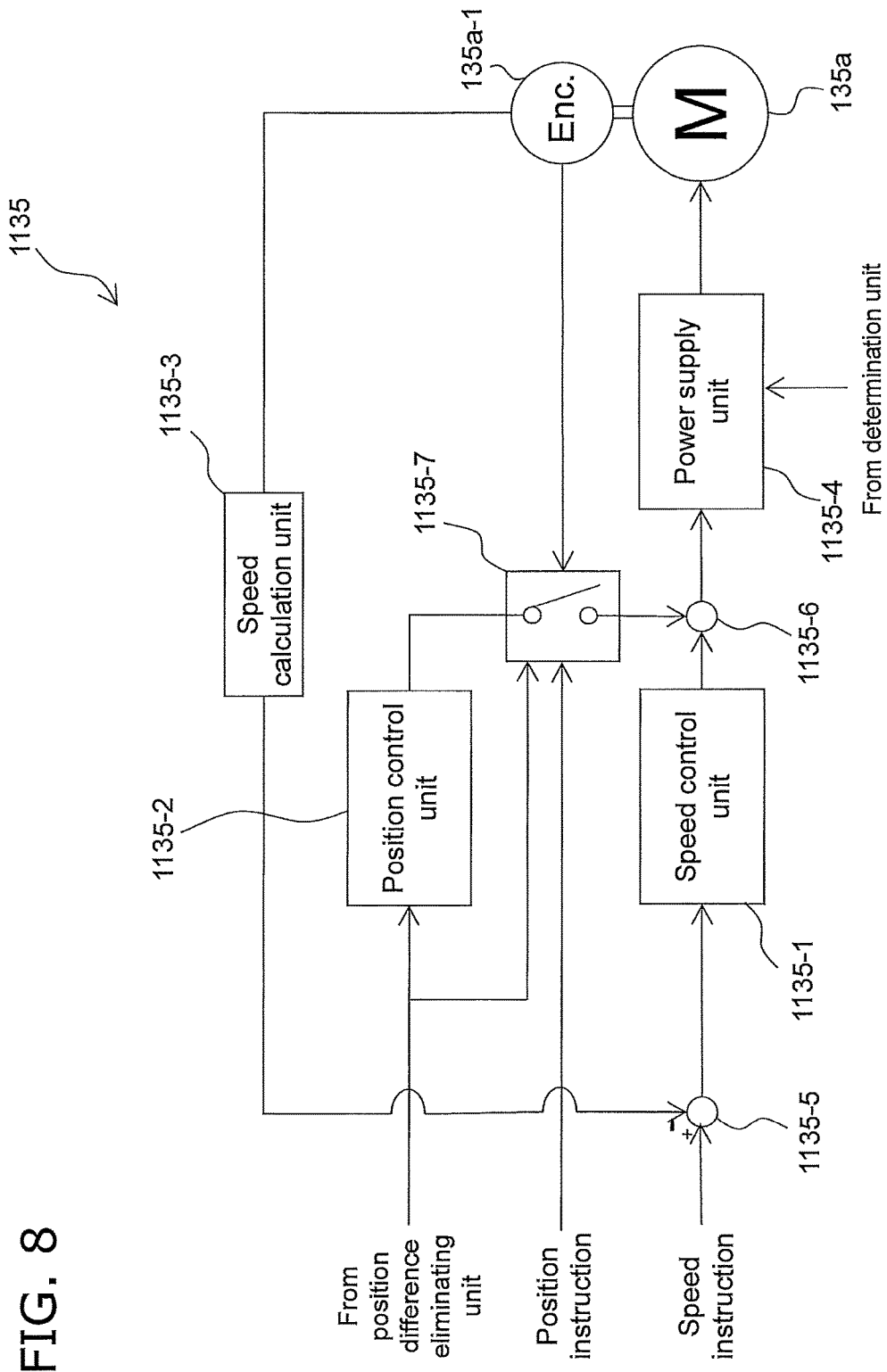
FIG. 8 is a diagram illustrating a structure of a motor drive unit.

Next, a structure of the motor drive unit 1135 is described with reference to FIG. 8. FIG. 8 is a diagram illustrating a structure of the motor drive unit. The motor drive unit 1135 includes a speed control unit 1135-1, the position control unit 1135-2, a speed calculation unit 1135-3, a power supply unit 1135-4 (described later), a difference calculation unit 1135-5 (described later), a combining unit 1135-6 (described later), and a switching unit 1135-7 (described later).

The speed control unit 1135-1 is connected to the difference calculation unit 1135-5 in a manner capable of transmitting and receiving signals. Accordingly, the speed control unit 1135-1 receives a difference (speed difference) between the speed instructed by the speed instruction (instructed speed) and an actual speed of the Y-axis direction tilt motor 135a, which is calculated by the difference calculation unit 1135-5.

Further, the speed control unit 1135-1 calculates the first control amount for controlling the power supply unit 1135-4 on the basis of the received speed difference. In this case, the speed control unit 1135-1 calculates the first control amount so as to eliminate the received speed difference. In other words, the speed control unit 1135-1 calculates the first control amount such that the actual motor speed follows the instructed speed.

As the speed control unit 1135-1, it is possible to use a control device that calculates a control amount such as to eliminate the speed difference on the basis of a control theory, for example. As this control device, there is a control device using a proportional integral differential (PID) control theory, for example. In this embodiment, a control device using a proportional integral (PI) control theory is used as the speed control unit 1135-1.

When the speed control unit 1135-1 is the control device using the PI control theory, the first control amount is expressed as $K_{pv} \times \Delta v + K_{iv} \times \text{Int}(\Delta v)$, where $\Delta v$ represents the speed difference, $\text{Int}(\Delta v)$ represents an integrated value over time of the speed difference $\Delta v$, and $K_{pv}$ and $K_{iv}$ are constants called control gains.

The position control unit 1135-2 is connected to the first difference calculation unit 1133 in a manner capable of transmitting and receiving signals. Accordingly, the position control unit 1135-2 receives the corrected position difference output from the position difference eliminating unit 1133. Further, position control unit 1135-2 calculates the second control amount for controlling the power supply unit 1135-4 so as to eliminate the corrected position difference output from the position difference eliminating unit 1133.

As the position control unit 1135-2, similarly to the speed control unit 1135-1, a control device that performs control based on a control theory can be used. In this embodiment, a control device using the PI control theory is used as the position control unit 1135-2.

In this case, the second control amount is expressed as $K_{pp} \times \Delta\theta + K_{ip} \times \mathrm{Int}(\Delta\theta)$, where $\Delta\theta$ represents the position difference, $\mathrm{Int}(\Delta\theta)$ represents an integrated value over time of the position difference $\Delta\theta$, and $K_{pp}$ and $K_{ip}$ are constants called control gains.

The speed calculation unit 1135-3 is connected to the first rotation information detection sensor 135a-1 in a manner capable of transmitting and receiving signals. In this way, the speed calculation unit 1135-3 calculates the rotation speed of the Y-axis direction tilt motor 135a from the pulse signal output from the first rotation information detection sensor 135a-1. The rotation speed of the Y-axis direction tilt motor 135a can be calculated from the number of pulses per unit time in the pulse signal, for example.

The power supply unit 1135-4 is connected to the speed control unit 1135-1 via the combining unit 1135-6. In addition, the power supply unit 1135-4 is connected to the position control unit 1135-2 via the combining unit 1135-6 and the switching unit 1135-7.

In this way, only the first control amount output from the speed control unit 1135-1 is input to the power supply unit 1135-4, or the first control amount and the second control amount output from the position control unit 1135-2 are combined by the combining unit 1135-6 and input to the power supply unit 1135-4.

When only the first control amount is input to the power supply unit 1135-4, the power supply unit 1135-4 outputs the feedback current on the basis of only the first control amount such that the speed (rotation speed) of the Y-axis direction tilt motor 135a follows the instructed speed. In this way, the motor drive unit 1135 can drive the Y-axis direction tilt motor 135a so that the rotation speed of the motor follows the instructed speed.

On the other hand, when the first control amount and the second control amount are combined by the combining unit 1135-6 and input to the power supply unit 1135-4, the power supply unit 1135-4 outputs the feedback current such that the rotation speed of the motor follows the instructed speed and that the tilt angle of the training rod 3 follows the instructed tilt angle. In this way, the motor drive unit 1135 can drive the Y-axis direction tilt motor 135a not only so that the rotation speed of the motor follows the instructed speed but also so that the tilt angle of the training rod 3 follows the instructed tilt angle.

Further, in this embodiment, the power supply unit 1135-4 outputs the current (feedback current) controlled based on the first control amount and/or second control amount. However, output from the power supply unit 1135-4 is not limited to the feedback current. For instance, the power supply unit 1135-4 may output a voltage whose voltage value and/or duty ratio are controlled on the basis of the first control amount and/or second control amount.

In addition, the power supply unit 1135-4 may be connected to the determination unit 1134. Further, the power supply unit 1135-4 may control the feedback current or voltage output from the power supply unit 1135-4 on the basis of true or false of the first condition described above.

For instance, it is possible not to set a limit to the current value or the voltage value output from the power supply unit 1135-4 if the first condition is "true", while to set an upper limit to the current value or the voltage value output that can be output from the power supply unit 1135-4 if the first condition is "false".

In this way, if the position difference change amount generated in the second time period $T_2$ is the first threshold $\phi_1$ or lower (if the first condition is "true"), the Y-axis direction tilt motor 135a can be controlled so that the position difference is accumulated and maintained.

On the other hand, if the position difference change amount generated in the second time period $T_2$ is higher than the first threshold $\phi_1$ (if the first condition is "false"), the feedback current or voltage value input to the Y-axis direction tilt motor 135a can be limited. As a result, when the determination unit 1134 determines an error, the torque output from the Y-axis direction tilt motor 135a can be limited.

The difference calculation unit 1135-5 has two inputs (an input denoted by "+" and an input denoted by "−"). The input denoted by "+" of the difference calculation unit 1135-5 is connected to the instruction generation unit 111 in a manner capable of transmitting and receiving signals. In this way, the speed instruction is input to the input denoted by "+" of the difference calculation unit 1135-5.

In addition, the input denoted by "−" of the difference calculation unit 1135-5 is connected to an output of the speed calculation unit 1135-3 in a manner capable of transmitting and receiving signals. In this way, the rotation speed of the Y-axis direction tilt motor 135a is input to the input denoted by "−" of the difference calculation unit 1135-5. Thus, the difference calculation unit 1135-5 calculates the difference between the instructed speed instructed by the speed instruction and the rotation speed of the Y-axis direction tilt motor 135a, namely the speed difference.

The combining unit 1135-6 combines the first control amount output from the speed control unit 1135-1 and the second control amount output from the position control unit 1135-2 (combined control amount) and outputs the result to the power supply unit 1135-4. Here, the combined control amount is a control amount obtained by adding the first control amount and the second control amount after appropriate weighting. By appropriately adjusting the weighting on the first control amount and the weighting on the second control amount, it is possible to adjust whether to put importance on the control so that the rotation speed of the Y-axis direction tilt motor 135a follows the instructed speed (speed control) or on the control so that the tilt angle of the training rod 3 follows the instructed tilt angle (position control).

The switching unit 1135-7 is connected to the output of the position control unit 1135-2 and one of inputs of the combining unit 1135-6. In addition, the switching unit 1135-7 is connected to the instruction generation unit 111 for generating the position instruction and the first rotation information detection sensor 135a-1 in a manner capable of transmitting and receiving signals. In this way, the switching unit 1135-7 can determine whether or not the number of pulses output from the first rotation information detection sensor 135a-1 (namely, the tilt angle of the training rod 3) has become a value corresponding to the deceleration start position instructed by the speed instruction and/or position instruction. Further, when the tilt angle of the training rod 3 has become the value corresponding to the deceleration start position instructed by the speed instruction, the switching unit 1135-7 can connect the output of the position control unit 1135-2 to the combining unit 1135-6 in a manner capable of transmitting and receiving signals. In other words, when the amount of rotation of the Y-axis direction tilt motor 135a has becomes the value corresponding to the deceleration start position instructed by the speed instruction, the switching unit 1135-7 enables the combining unit 1135-6 to receive the second control amount that is the output of the position control unit 1135-2.

In this way, only when the speed instruction is the deceleration instruction, the switching unit 1135-7 can reflect the second control amount output from the position control unit 1135-2 on the control of the Y-axis direction tilt motor 135a. As a result, the training rod 3 can reach the target tilt angle with a difference as small as possible.

In addition, the switching unit 1135-7 is connected to the position difference eliminating unit 1133 in a manner capable of transmitting and receiving signals. For this reason, when the position difference eliminating unit 1133 resets the accumulated and maintained position difference, the switching unit 1135-7 can connect the output of the position control unit 1135-2 to the combining unit 1135-6 in a manner capable of transmitting and receiving signals. In this way, when the position difference eliminating unit 1133 physically resets the accumulated and maintained position difference, it is possible to reflect the second control amount output from the position control unit 1135-2 on calculation of the feedback current value. As a result, the Y-axis direction tilt motor 135a can be controlled so that the tilt angle of the training rod 3 follows the instructed tilt angle. Further, the difference (the position difference) between the actual tilt angle of the training rod 3 and the instructed angle can be physically reset.

(5) Operation of Training Apparatus

I. Basic Operation of Training Apparatus

Figure 9:
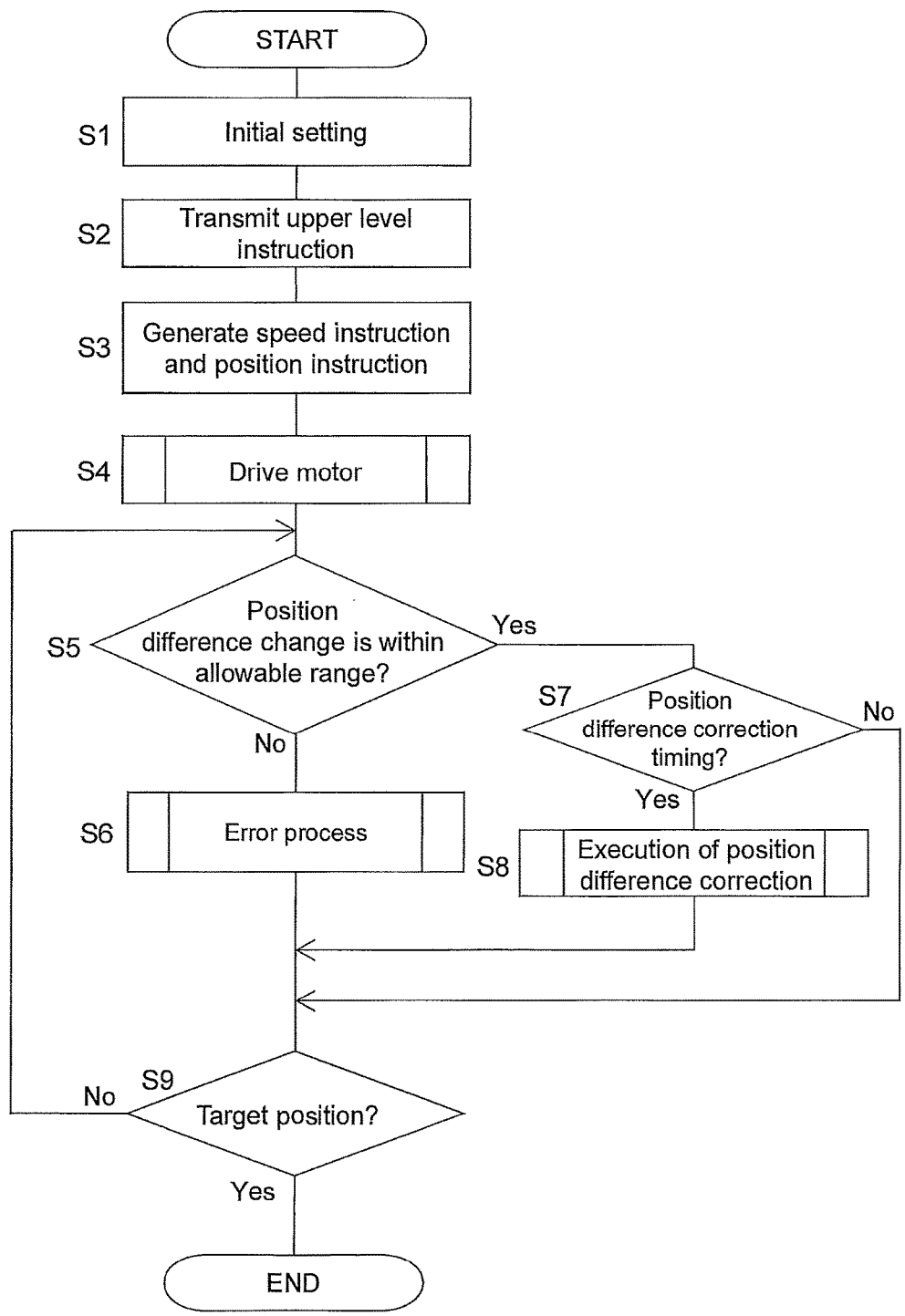
FIG. 9 is a flowchart illustrating a basic operation of the training apparatus.

Next, an operation of the training apparatus 100 is described. First, a basic operation of the training apparatus 100 is described with reference to FIG. 9. FIG. 9 is a flowchart illustrating a basic operation of the training apparatus 100. Further, in the following description, an operation of the training apparatus 100 when the training mode is set to the guided mode is exemplified for describing the operation of the training apparatus 100. In addition, an operation in which the Y-axis direction tilt motor 135a is controlled by the motor control unit 113a is exemplified for describing the operation of the training apparatus 100. It is because that the control is performed also when the X-axis direction tilt motor 135b and the expansion/contraction motor 359 are controlled by the motor control units 113b and the 113c, respectively.

First, the user makes various initial settings of the training apparatus 100 by using the training instruction unit 5 and the like (Step S1). In this case, the user of the training apparatus 100 sets the training mode to the guided mode by using the training instruction unit 5. Further, the user of the training apparatus 100 sets the training program of the limb of the patient in the guided mode by using the training instruction unit 5.

Next, the training instruction unit 5 generates the training rod operation instruction on the basis of the set training program. After that, the training instruction unit 5 transmits the training rod operation instruction (upper level instruction) to the instruction generation unit 111 of the control unit 11 (Step S2).

The instruction generation unit 111, which has received the training rod operation instruction, generates the speed instruction and the position instruction on the basis of the target position information, the target speed information, and the acceleration rate information included in the training rod operation instruction (Step S3).

After the instruction generation unit 111 generates the speed instruction and/or position instruction, the motor control unit 113a controls the Y-axis direction tilt motor 135a on the basis of the speed instruction and/or the position instruction (Step S4). Details of the drive of the Y-axis direction tilt motor 135a by the motor control unit 113a in this embodiment will be described later.

After the motor control unit 113a starts the drive of the Y-axis direction tilt motor 135a, the determination unit 1134 first determines whether or not the position difference change amount generated in the second time period $T_2$ is the first threshold $\phi_1$ or lower (Step S5).

If the position difference change amount generated in the second time period $T_2$ is the first threshold $\phi_1$ or lower ("Yes" in Step S5), the process proceeds to Step S7. On the other hand, if the position difference change amount generated in the second time period $T_2$ is higher than the first threshold $\phi_1$ ("No" in Step S5), the process proceeds to Step S6.

A method of determining the position difference change amount in Step S5 will be described in detail.

If the position difference change amount generated in the second time period $T_2$ is higher than the first threshold $\phi_1$ ("No" in Step S5), the determination unit 1134 determines that an error has occurred (Step S6). In this case, the determination unit 1134 instructs the training instruction unit 5 to provide visual or auditory information and the like to the user (the patient and the like) as necessary. In addition, the determination unit 1134 instructs the motor control unit 113a to perform an appropriate error process considering safety. For instance, the determination unit 1134 instructs the motor drive unit 1135 to stop rotation of the Y-axis direction tilt motor 135a.

Alternatively, the determination unit 1134 may instruct the motor drive unit 1135 to perform control of limiting an upper limit of the torque that can be output from the Y-axis direction tilt motor 135a. In this case, the motor drive unit 1135 limits the feedback current or voltage input to the Y-axis direction tilt motor 135a. In this way, if the position difference change amount generated in the second time period $T_2$ is higher than the first threshold $\phi_1$, i.e., if the position difference change amount per unit time is excessive, the torque of the Y-axis direction tilt motor 135a is limited. As a result, the training rod 3 is prevented from applying an excessive load on the limb of the patient.

After the error process is performed, the process proceeds to Step S9.

If the position difference change amount generated in the second time period $T_2$ is the first threshold $\phi_1$ or lower ("Yes" in Step S5), the position difference eliminating unit 1133 monitors whether or not it is a timing for performing position difference correction (Step S7). In this embodiment, the position difference eliminating unit 1133 monitors (i) whether or not the determination unit 1134 determines that the position difference change amount generated in the third time period $T_3$ is the second threshold $\phi_2$ or lower, (ii) whether or not the operation of the training rod 3 (the Y-axis direction tilt motor 135a) has stopped, and (iii) whether or not the actual tilt angle of the training rod 3 has reached the deceleration start position (described later). A specific method of monitoring the three timings by the position difference eliminating unit 1133 will be described later.

If the position difference eliminating unit 1133 determines that it is not the timing for performing the position difference correction ("No" in Step S7), the process proceeds to Step S9.

On the other hand, if the position difference eliminating unit 1133 determines that it is the timing for performing the position difference correction ("Yes" in Step S7), the process proceeds to Step S8.

If the position difference eliminating unit 1133 determines that it is the timing for performing the position difference correction ("Yes" in Step S7), the position difference eliminating unit 1133 resets the accumulated and maintained position difference (Step S8). The position difference eliminating unit 1133 resets the position difference by (i) a method of physically resetting the position difference, and/or (ii) a method of setting the position difference value as the parameter handled by the control unit 11 to zero. Methods (i) and (ii) of resetting the position difference will be described later in detail.

After the error process in Step S6, after resetting the position difference in Step S8, or if the position difference eliminating unit 1133 determines that it is not the timing for performing the position difference correction in Step S7 ("No" in Step S7), the motor control unit 113a determines whether or not the training rod 3 has reached the target tilt angle to be finally reached by the training rod 3 (Step S9). If the tilt angle of the training rod 3 is the target tilt angle ("Yes" in Step S9), the control of the Y-axis direction tilt motor 135a by the motor control unit 113a is finished.

Further, if it is determined in Step S9 that the tilt angle of the training rod 3 is the target tilt angle, the motor control unit 113a instructs the training instruction unit 5 to inform the user such as the patient that the tilt angle of the training rod 3 has reached the target tilt angle, using visual or auditory information. In this way, the patient can maintain motivation to continue the training.

On the other hand, if the tilt angle of the training rod 3 has not reached the target tilt angle ("No" in Step S9), the process returns to Step S5.

Further, whether or not the training rod 3 has reached the target tilt angle may be determined on the basis of the number of pulses output from the first rotation information detection sensor 135a-1, or on the basis of whether or not all speed instructions and/or position instructions have been performed.

II. Motor Control Method

Figure 10:
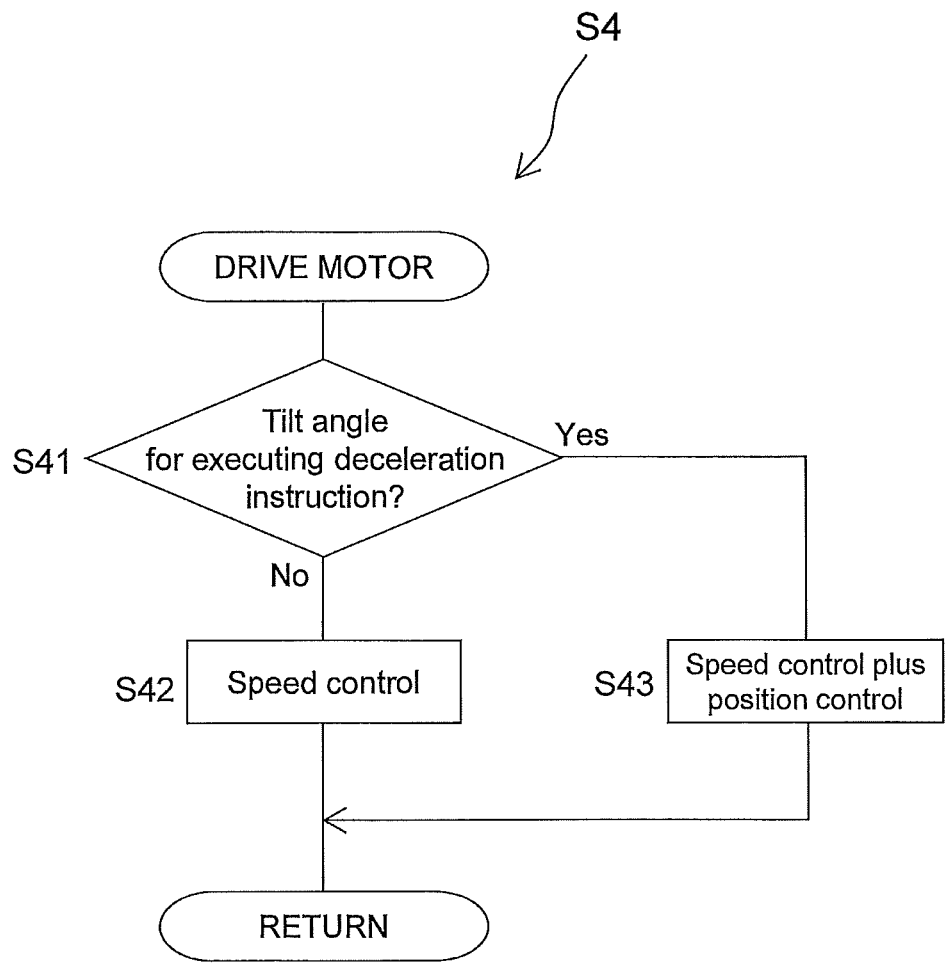
FIG. 10 is a flowchart illustrating a method of controlling a motor.

Next, the method of controlling the motor in Step S4 of FIG. 9 in this embodiment is described with reference to FIG. 10. FIG. 10 is a flowchart illustrating the method of controlling the motor.

When starting the drive of the Y-axis direction tilt motor 135a, the switching unit 1135-7 first calculates the actual tilt angle of the training rod 3 from the number of pulses output from the first rotation information detection sensor 135a-1. Further, it is checked whether or not the calculated tilt angle of the training rod 3 is the tilt angle at which the deceleration instruction of the speed instruction should be executed (Step S41). In this way, because it is determined whether or not the deceleration instruction of the speed instruction should be executed on the basis of the actual tilt angle of the training rod 3, the deceleration can be started at an appropriate timing. As a result, the training rod 3 can be accurately moved to the target tilt angle with a difference as small as possible.

If the actual tilt angle of the training rod 3 has not reached the tilt angle at which the deceleration instruction should be executed ("No" in Step S41), the process proceeds to Step S42. On the other hand, if the actual tilt angle of the training rod 3 has reached the tilt angle at which the deceleration instruction should be executed ("Yes" in Step S41), the process proceeds to Step S43.

If it is determined in Step S41 that the actual tilt angle of the training rod 3 has not reached the tilt angle at which the deceleration instruction should be executed ("No" in Step S41), the switching unit 1135-7 disconnect the position control unit 1135-2 from the combining unit 1135-6 in a manner in which a signal cannot transmitted and received, so that the second control amount output from the position control unit 1135-2 is not input to the combining unit 1135-6 (Step S42). In this way, only the first control amount output from the speed control unit 1135-1 is reflected when the power supply unit 1135-4 outputs the feedback current. As a result, the motor drive unit 1135 controls the Y-axis direction tilt motor 135a so that the rotation speed of the Y-axis direction tilt motor 135a follows only the instructed speed (speed control).

If the actual tilt angle of the training rod 3 has not reached the tilt angle at which the deceleration instruction should be executed, the acceleration instruction or the constant speed instruction of the speed instruction is executed as illustrated in FIGS. 5A, 5B and 6. Accordingly, when the acceleration instruction or the constant speed instruction of the speed instruction is executed, the motor drive unit 1135 controls the Y-axis direction tilt motor 135a so that the rotation speed of the Y-axis direction tilt motor 135a follows only the instructed speed.

In addition, when the Y-axis direction tilt motor 135a is controlled so that the rotation speed of the Y-axis direction tilt motor 135a follows only the instructed speed, the rotation speed of the Y-axis direction tilt motor 135a follows the instructed speed (namely, the speed difference is canceled), while the position difference is not canceled but is accumulated and maintained. It is because that when the power supply unit 1135-4 calculates the feedback current in the speed control, the second control amount is not reflected.

Figure 11:
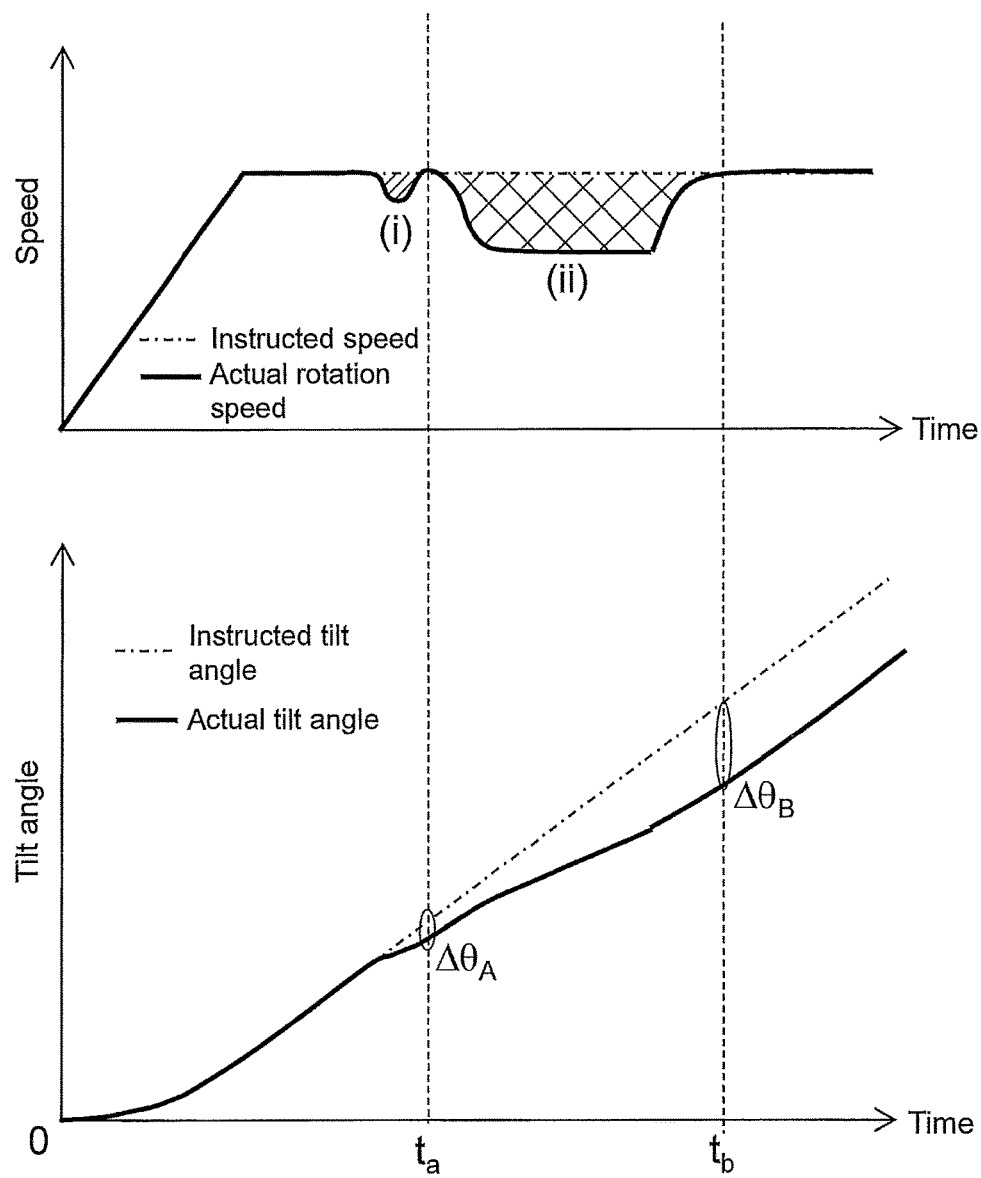
FIG. 11 is a diagram illustrating a manner in which a speed difference is canceled, while a position difference is accumulated and maintained.

FIG. 11 illustrates a manner in which the speed difference is canceled while the position difference is accumulated and maintained. As illustrated in FIG. 11, the speed difference (i) in FIG. 11 is canceled at a time point $t_a$ by the speed control. At the time point $t_a$ at which the speed difference (i) is canceled, a position difference $\Delta\theta_A$ corresponding to a time integration of the speed difference (i) (an area of the region illustrated by hatching in the graph) is generated. In this case, because the position control unit 1135-2 is disconnected from the combining unit 1135-6, the second control amount is not reflected when the feedback current is calculated. As a result, the position difference $\Delta\theta_A$ is not canceled but is maintained. In addition, the speed difference (ii) that is secondly generated is canceled at a time point $t_b$ by the speed control. Further, at the time point $t_b$ at which the speed difference (ii) is canceled, a position difference corresponding to a time integration of the speed difference (ii) (an area of the region illustrated by crosshatching in the graph) is generated. Here, because the position difference $\Delta\theta_A$ is not canceled but is maintained, at the time point $t_b$ at which the speed difference (ii) is canceled, the position difference generated by the speed difference (ii) and the position difference $\Delta\theta_A$ generated by the speed difference (i) are accumulated so that a position difference $\Delta\theta_B$ is generated. Further, if the speed difference is not generated after the time point $t_b$, the position difference $\Delta\theta_B$ is not changed and is maintained. On the other hand, if the speed difference is generated after the time point $t_b$, the position difference generated due to occurrence of the speed difference is accumulated to $\Delta\theta_B$.

In the training apparatus 100, it is preferred for the patient to continue the training even if the position difference is generated in some amount as long as the movement of the limb of the patient can follow the movement of the training rod 3 indicated by the training rod operation instruction in a certain degree. Accordingly, in this embodiment, when the acceleration instruction and/or the constant speed instruction of the speed instruction are executed, the Y-axis direction tilt motor 135a is controlled only by the speed control. In this way, the Y-axis direction tilt motor 135a can be controlled so as to follow the speed instruction without canceling the position difference. As a result, even if there is the position difference in some amount, the moving speed of the training rod 3 can follow the moving speed indicated in the training rod operation instruction while the patient can continue the training of the limb.

On the other hand, if it is determined that the actual tilt angle of the training rod 3 is the tilt angle at which the deceleration instruction should be executed ("Yes" in Step S41), a switching unit 1135-7 connects the position control unit 1135-2 to the combining unit 1135-6 in a manner capable of transmitting and receiving signals (Step S43). In other words, the second control amount output from the position control unit 1135-2 can be input to the combining unit 1135-6. In this way, when the deceleration instruction is executed, not only the first control amount but also the second control amount is reflected when the power supply unit 1135-4 outputs the feedback current. In this way, when the deceleration instruction is executed, the actual tilt angle of the training rod 3 follows the instructed tilt angle, too. Accordingly, the training rod 3 can accurately reach the target tilt angle.

When the motor control unit 113a executes Steps S41 to S43 described above, the motor control unit 113a can control the Y-axis direction tilt motor 135a to follow only the speed instruction when the acceleration instruction and/or the constant speed instruction of the speed instruction is executed. Further, when the deceleration instruction is executed, the Y-axis direction tilt motor 135a can be controlled to follow the speed instruction and the position instruction.

Note that the motor control in Step S4 described above is executed until the training rod 3 reaches the target tilt angle, or until the operation of the training rod 3 is stopped due to occurrence of an error or user's instruction.

Figure 12:
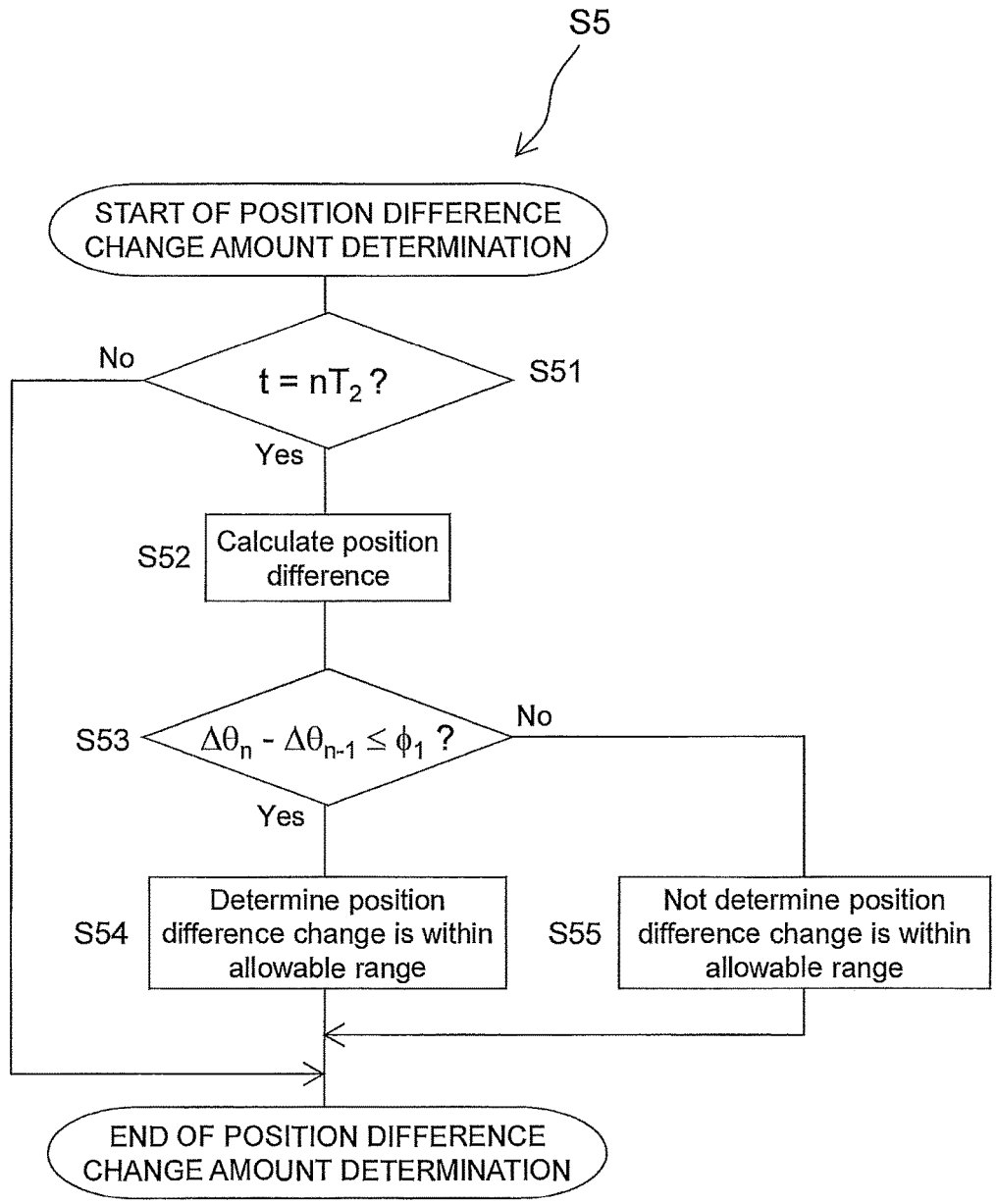
FIG. 12 is a flowchart illustrating a method of determining whether or not a position difference change amount is within an allowable range.

III. Method of Determining Whether or Not Position Difference Change Amount is Within Allowable Range Next, a method of determining whether or not the position difference change amount is within an allowable range in Step S5 of the flowchart illustrated in FIG. 9 is described with reference to FIG. 12. FIG. 12 is a flowchart illustrating the method of determining whether or not the position difference change amount is within an allowable range.

When the determination whether or not the position difference change amount is within an allowable range is started, the determination unit 1134 first determines whether or not an elapsed time t from start of the drive of the Y-axis direction tilt motor 135a is an multiple of the second time period $T_2$ and an integer (n) (Step S51). If the elapsed time t is not an integral multiple of the second time period $T_2$ ("No" in Step S51), the determination unit 1134 does not determine whether or not the position difference change amount is within the allowable range, and finishes the determination whether or not the position difference change amount is within the allowable range. Then, the process proceeds to Step S7.

On the other hand, if the elapsed time t is an integral multiple of the second time period $T_2$ ("Yes" in Step S51), the determination unit 1134 obtains the accumulated and maintained position difference from the position difference calculation unit 1132 (Step S52). Further, the determination unit 1134 regards the obtained position difference as an accumulated and maintained position difference $\Delta\theta_n$ at an elapsed time $t=nT_2$ and stores the same in the storage device of the motor control unit 113a or the like.

Note that the position difference calculation unit 1132 calculates the position difference at an interval of the first time period $T_1$. It is because that the position difference calculation unit 1132 is connected to the motor drive unit 1135 via the position difference eliminating unit 1133, and the motor drive unit 1135 controls the Y-axis direction tilt motor 135a on the basis of the position difference calculated by the position difference calculation unit 1132 (or corrected by the position difference eliminating unit 1133).

On the other hand, the second time period $T_2$ in which the determination unit 1134 obtains the position difference is a time interval for determining a position difference change amount per unit time. Accordingly, the second time period $T_2$ may be a time interval sufficiently longer than the first time period $T_1$. Because the second time period $T_2$ is a time interval sufficiently longer than the first time period $T_1$, a calculation load in the motor control unit 113a can be reduced.

Next, the determination unit 1134 determines whether or not the position difference generated per second time period $T_2$ is the first threshold $\phi_1$ or lower (Step S53). Specifically, the determination is performed as follows.

First, the determination unit 1134 reads out a position difference $\Delta\theta_{n-1}$ calculated last time, namely the position difference accumulated and maintained at the elapsed time $t=(n-1)T_2$ from the storage device of the motor control unit 113a or the like. Further, the determination unit 1134 calculates a difference $\Delta\theta_n - \Delta\theta_{n-1}$ between the position difference $\Delta\theta_n$ at the elapsed time $t=nT_2$ and the position difference $\Delta\theta_{n-1}$ at the elapsed time $t=(n-1)T_2$. In this way, the position difference change amount generated per second time period $T_2$ (namely, per unit time) is calculated at the elapsed time $t=nT_2$. After that, the determination unit 1134 determines whether or not $\Delta\theta_n - \Delta\theta_{n-1}$ is the first threshold $\phi_1$ or lower.

If $\Delta\theta_n - \Delta\theta_{n-1}$ is the first threshold $\phi_1$ or lower ("Yes" in Step S53), it is determined that the position difference change amount is within the allowable range (Step S54), and finishes determination whether or not the position difference change amount is within the allowable range. On the other hand, if $\Delta\theta_n - \Delta\theta_{n-1}$ is higher than first threshold $\phi_1$ ("No" in Step S53), it is determined that the position difference change amount is not within the allowable range (Step S55), and finishes the determination whether or not the position difference change amount is within the allowable range.

In this way, when the difference between the position difference obtained at a certain elapsed time and the position difference obtained the second time period $T_2$ before the certain elapsed time is calculated, the position difference change amount generated per the second time period $T_2$ can be calculated. Further, by determining whether or not the position difference change amount per the second time period $T_2$ is the first threshold $\phi_1$ or lower, the determination unit 1134 can determine whether the position difference generated per unit time (the position difference change amount per unit time) is a slow position difference change or a rapid position difference change.

Figure 13A:
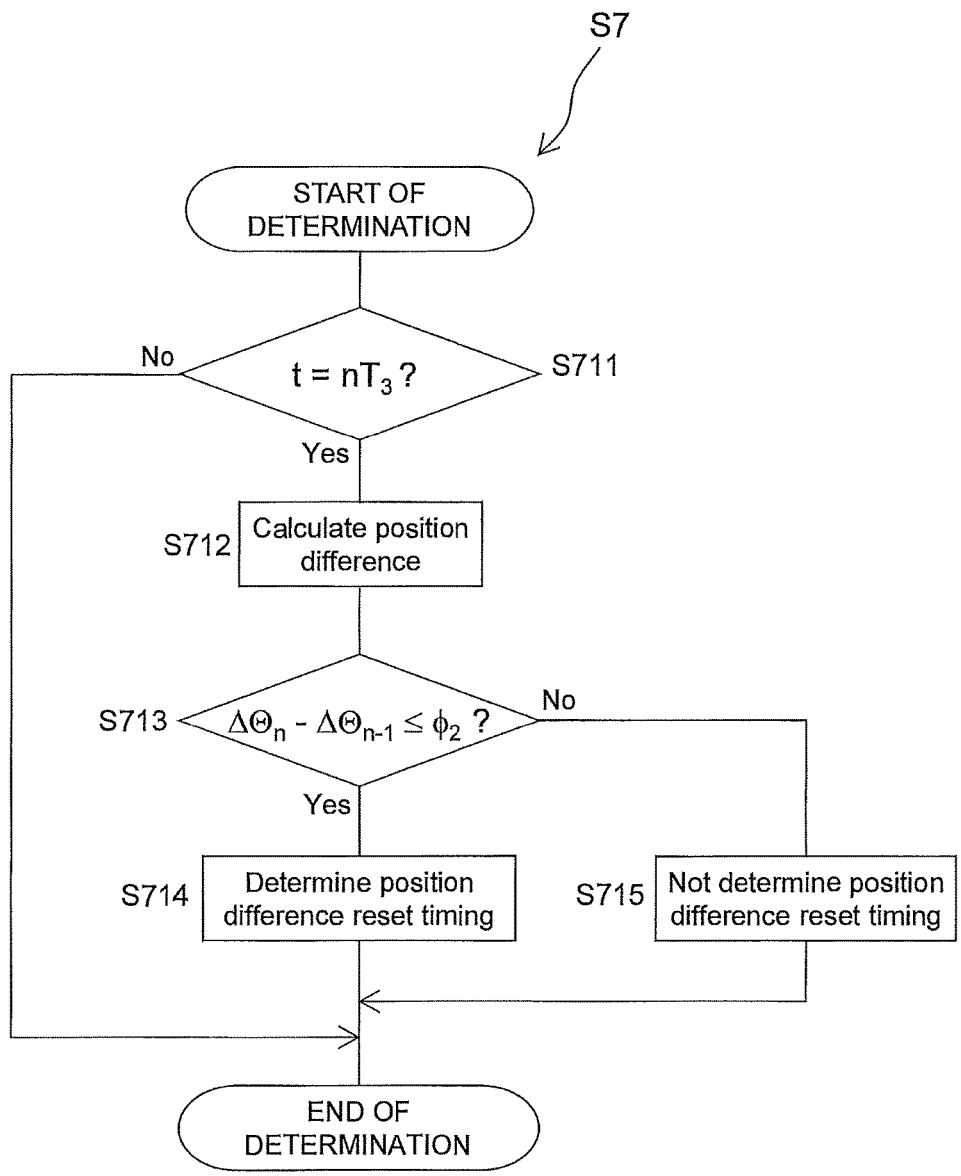
FIG. 13A is a flowchart illustrating a method of determining whether or not the position difference change amount generated in a third time period is a second threshold or lower.
Figure 13B:
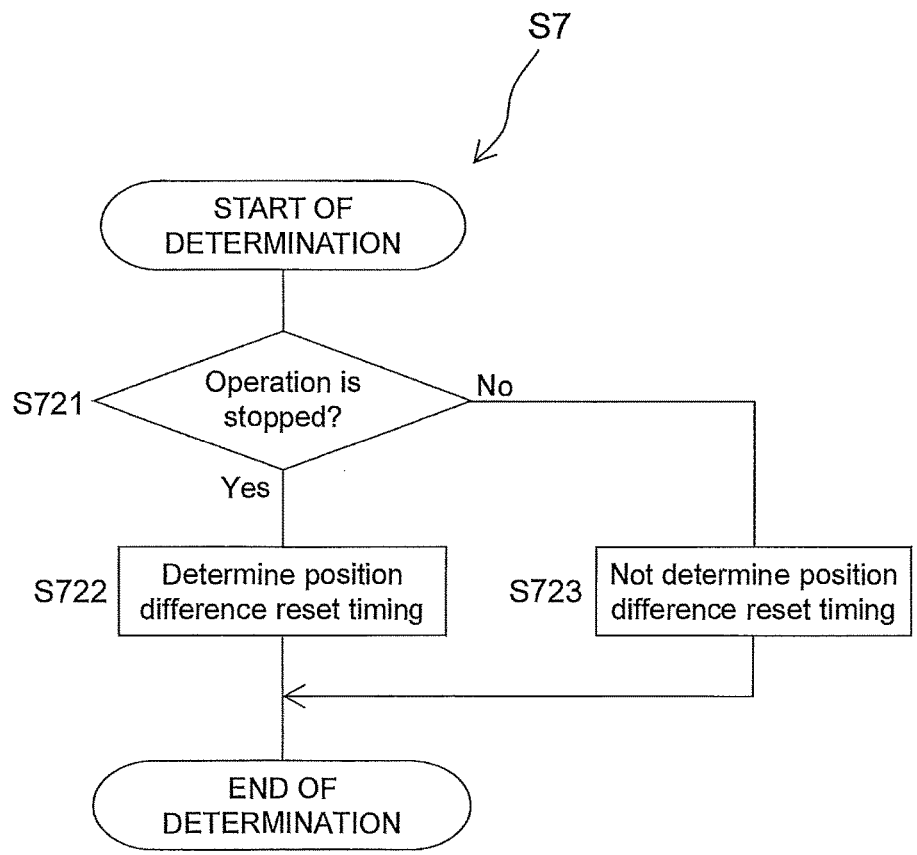
FIG. 13B is a flowchart illustrating a method of determining whether or not operation of the training rod is stopped.
Figure 13C:
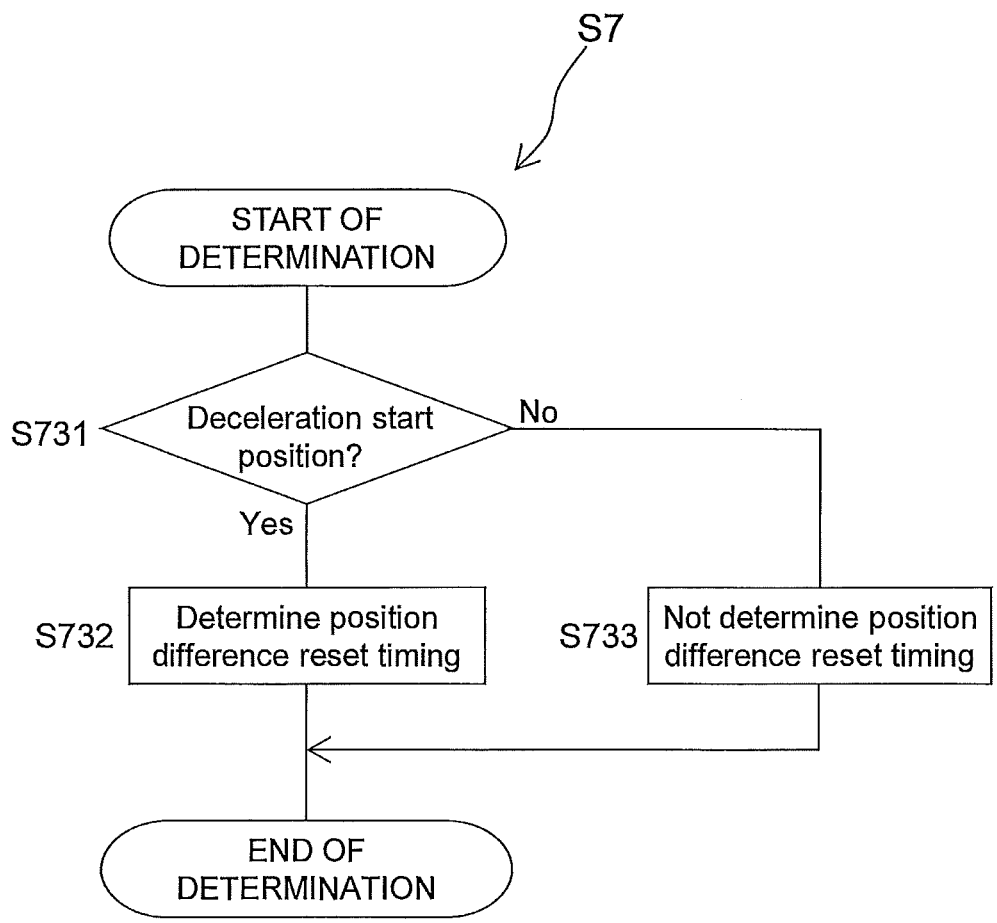
FIG. 13C is a flowchart illustrating a method of determining whether or not a tilt angle of the training rod has reached a deceleration start position.

IV. Method of Determining Timing for Performing Correction (Reset) of Position Difference Next, a method of determining the timing for performing the correction (reset) of the position difference in Step S7 will be described with reference to FIGS. 13A to 13C. The timing of the correction (reset) of the position difference in Step S7 is (i) whether or not the determination unit 1134 determines that the position difference change amount generated in the third time period $T_3$ is the second threshold $\phi_2$ or lower, (ii) whether or not operation of the training rod 3 (the Y-axis direction tilt motor 135a) has stopped, or (iii) whether or not the actual tilt angle of the training rod 3 has reached the deceleration start position. Each method of determining the timing is explained below. FIG. 13A is a flowchart illustrating the method of determining whether or not the position difference change amount generated in the third time period $T_3$ is the second threshold $\phi_2$ or lower. FIG. 13B is a flowchart illustrating a method of determining whether or not the operation of the training rod 3 (or the Y-axis direction tilt motor 135a) is stopped. FIG. 13C is a determining illustrating a method of determining whether or not the tilt angle of the training rod 3 has reached the deceleration start position.

(i) Method of Determining Whether or not Position Difference Change Amount Generated in Third Time Period $T_3$ is Second Threshold $\phi_2$ or Lower The method of determining whether or not the position difference change amount generated in the third time period $T_3$ is the second threshold $\phi_2$ or lower is described below with reference to FIG. 13A.

First, the determination unit 1134 determines whether or not the elapsed time t from start of the drive of the Y-axis direction tilt motor 135a is a multiple of the third time period $T_3$ and an integer (n) (Step S711). If the elapsed time t is not an integral multiple of the third time period $T_3$ ("No" in Step S711), the determination unit 1134 finishes the determination. Then, the process proceeds to Step S9.

On the other hand, if the elapsed time t is an integral multiple of the third time period $T_3$ ("Yes" in Step S711), the determination unit 1134 obtains the accumulated and maintained position difference from the position difference calculation unit 1132 (Step S712). Further, the determination unit 1134 regards the obtained position difference as the position difference $\Delta\Theta_n$ accumulated and maintained at the elapsed time t=$nT_3$, and stores the same in the storage device of the motor control unit 113a or the like.

Next, the determination unit 1134 determines whether or not the position difference change amount generated per the third time period $T_3$ is the second threshold $\phi_2$ or lower (Step S713). Specifically, the determination is performed as follows. First, the determination unit 1134 reads out the position difference $\Delta\Theta_{n-1}$ calculated last time, namely the position difference accumulated and maintained at the elapsed time t=$(n-1)T_3$ from the storage device of the motor control unit 113a or the like. Further, the determination unit 1134 calculates the difference $\Delta\Theta - \Delta\Theta_{n-1}$ between the position difference $\Delta\Theta_n$ at the elapsed time t=$nT_3$ and the position difference at the elapsed time t=$(n-1)T_3$. In this way, the position difference change amount generated per the third time period $T_3$ (namely, per unit time) is calculated at the elapsed time t=$nT_3$. After that, the determination unit 1134 determines whether or not $\Delta\Theta_n - \Delta\Theta_{n-1}$ is the second threshold $\phi_2$ or lower.

If $\Delta\Theta_n - \Delta\Theta_{n-1}$ is the second threshold $\phi_2$ or lower ("Yes" in Step S713), the determination unit 1134 determines that the position difference change amount per the third time period $T_3$ is the second threshold $\phi_2$ or lower, i.e., that it is the timing for performing the correction (reset) of the position difference (Step S714), and finishes the determination whether or not the position difference change amount per the third time period $T_3$ is the second threshold $\phi_2$ or lower. On the other hand, if $\Delta\Theta_n - \Delta\Theta_{n-1}$ is higher than the second threshold $\phi_2$ ("No" in Step S713), the determination unit 1134 determines that the position maintained position difference from the position difference calculation unit 1132 (Step S712). Further, the determination unit 1134 regards the obtained position difference as the position difference $\Delta\Theta_n$ accumulated and maintained at the elapsed time t=$nT_3$, and stores the same in the storage device of the motor control unit 113a or the like.

(ii) Method of Determining Whether or Not Operation of Training Rod (or Motor) is Stopped Next, a method of determining whether or not the operation of the training rod 3 (or the Y-axis direction tilt motor 135a) is stopped is described with reference to FIG. 13B.

First, the position difference eliminating unit 1133 determines whether or not the operation of the training rod 3 is stopped (Step S721). Whether or not the operation of the training rod 3 is stopped is determined on the basis of (i) whether or not the tilt angle of the training rod 3 is not substantially changed (when the patient has instructed to stop), (ii) whether or not the training rod 3 has reached the target tilt angle instructed by the position instruction, and/or, (iii) whether or not the speed instruction is all executed.

If the determination is performed on the basis of the tilt angle of the training rod 3 as (i) and (ii) described above, the position difference eliminating unit 1133 subtracts the position difference calculated by the position difference calculation unit 1132 from the instructed tilt angle instructed by the position instruction so as to calculate the actual tilt angle of the training rod 3. Other than that, the position difference eliminating unit 1133 may obtain the tilt angle of the training rod 3 directly from the tilt angle calculation unit 1131.

Whether or not the tilt angle of the training rod 3 is not changed as (i) described above can be determined on the basis of whether or not the actual tilt angle of the training rod 3 calculated by the position difference eliminating unit 1133 has changed in a predetermined time period.

Whether or not the training rod 3 has reached the target tilt angle instructed by the position instruction as (ii) described above can be determined on the basis of whether or not the actual tilt angle of the training rod 3 calculated by the position difference eliminating unit 1133 is the same as the target tilt angle.

Whether or not the speed instruction is all executed as (iii) described above can be determined, for example, on the basis of whether or not the elapsed time t from the start of the drive of the Y-axis direction tilt motor 135a becomes an elapsed time $t_5$ (in the case of the speed instruction of FIG. 5A) or the elapsed time $t_3$ (in the case of the speed instruction of FIG. 5B) indicated in the speed instruction illustrated in FIGS. 5A and 5B.

If the position difference eliminating unit 1133 determines that the operation of the training rod 3 is stopped ("Yes" in Step S721), it is determined to be the timing to correct (reset) the accumulated and maintained position difference (Step S722), and the determination is finished. On the other hand, if the position difference eliminating unit 1133 determines that the operation of the training rod 3 is not stopped ("No" in Step S721), it is determined not to be the timing to correct (reset) the accumulated and maintained position difference (Step S723), and the determination is finished.

Other than that, the position difference eliminating unit 1133 may directly monitor the rotation speed of the Y-axis direction tilt motor 135a calculated by the speed calculation unit 1135-3, so as to determine that the operation of the training rod 3 is stopped when the rotation speed becomes zero (or a predetermined value close to zero).

(iii) Method of Determining Whether or Not Tilt Angle of Training Rod has Reached Deceleration Start Position Next, a method of determining whether or not the tilt angle of the training rod 3 has reached the deceleration start position is described with reference to FIG. 13C.

First, the position difference eliminating unit 1133 determines whether or not the tilt angle of the training rod 3 has reached the deceleration start position of the Y-axis direction tilt motor 135a (Step S731). Whether or not the tilt angle of the training rod 3 has reached the deceleration start position is determined on the basis of whether or not the tilt angle of the training rod 3 is the same as an instructed tilt angle $\theta_d$ at the elapsed time $t_2$ in the position instruction illustrated in FIG. 6. Here, whether or not to be the deceleration start position of the Y-axis direction tilt motor 135a is not determined on the basis of the elapsed time t from the start of the drive of the Y-axis direction tilt motor 135a (namely, on the basis of whether or not the elapsed time t is equal to $t_2$).

If it is determined whether or not to be the deceleration start position of the Y-axis direction tilt motor 135a on the basis of whether or not the elapsed time t from the start of the drive of the Y-axis direction tilt motor 135a is equal to $t_2$, unintentional reset of the position difference may be performed when the acceleration instruction or the constant speed instruction of the speed instruction is executed.

For instance, if a position difference occurs when the acceleration instruction or the constant speed instruction is executed, the actual tilt angle of the training rod 3 has not reached the deceleration start position $\theta_d$ instructed by the speed instruction (position instruction) at the time point when the elapsed time t is $t_2$. In this case, even if the elapsed time t is $t_2$, the acceleration instruction or the constant speed instruction is executed. In this way, if the position difference is simply reset at the elapsed time $t_2$, the position difference is reset before the actual tilt angle of the training rod 3 reaches the deceleration start position, which is unintentional reset of the position difference.

Accordingly, the deceleration instruction is executed after the actual tilt angle of the training rod 3 reaches the deceleration start position $\theta_d$ instructed by the speed instruction (position instruction), and hence the unintentional stop of the training rod 3 can be prevented.

In addition, the timing to reset the position difference is determined on the basis of whether or not the actual tilt angle of the training rod 3 is equal to the deceleration start position $\theta_d$, and hence it is possible to avoid the unintentional reset of the position difference when the acceleration instruction or the constant speed instruction is executed.

If the position difference eliminating unit 1133 determines that the actual tilt angle of the training rod 3 is equal to the deceleration start position $\theta_d$ ("Yes" in Step S731), it is determine to be the timing to correct (reset) the accumulated and maintained position difference (Step S732), and the determination is finished. On the other hand, if the position difference eliminating unit 1133 determines that the tilt angle of the training rod 3 is not equal to the deceleration start position $\theta_d$ ("No" in Step S731), it is determined not to be the timing to correct (reset) the position difference (Step S733), and the determination is finished.

V. Method of Position Difference Correction

Figure 14A:
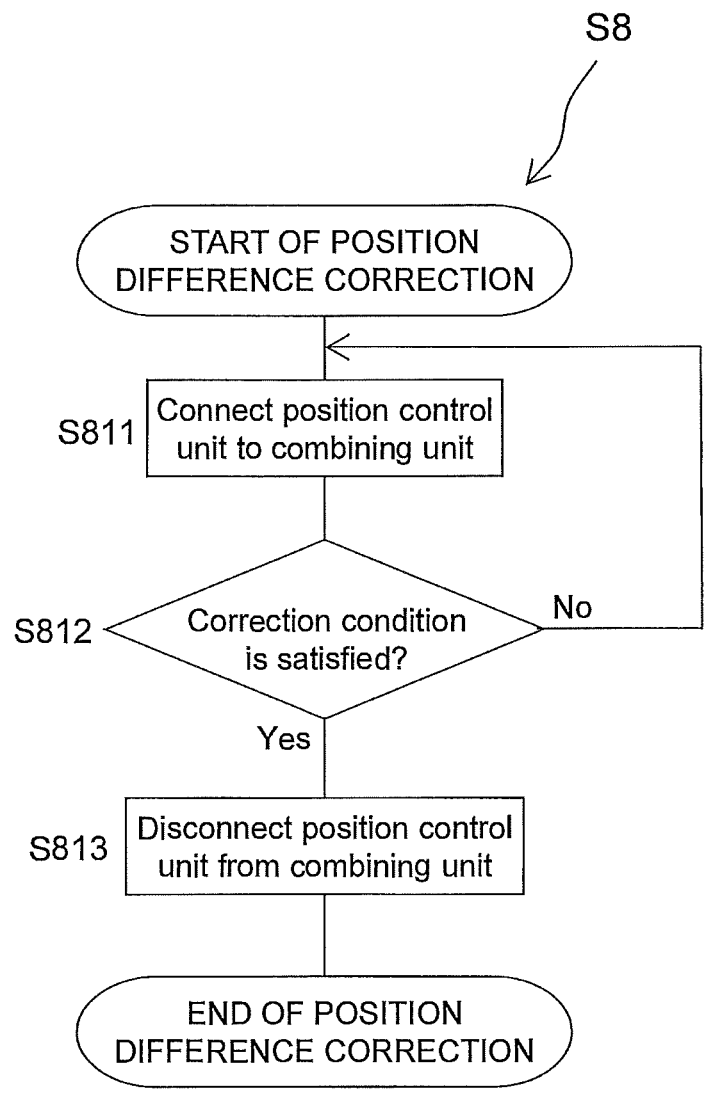
FIG. 14A is a flowchart illustrating a method of physically resetting the position difference.
Figure 14B:
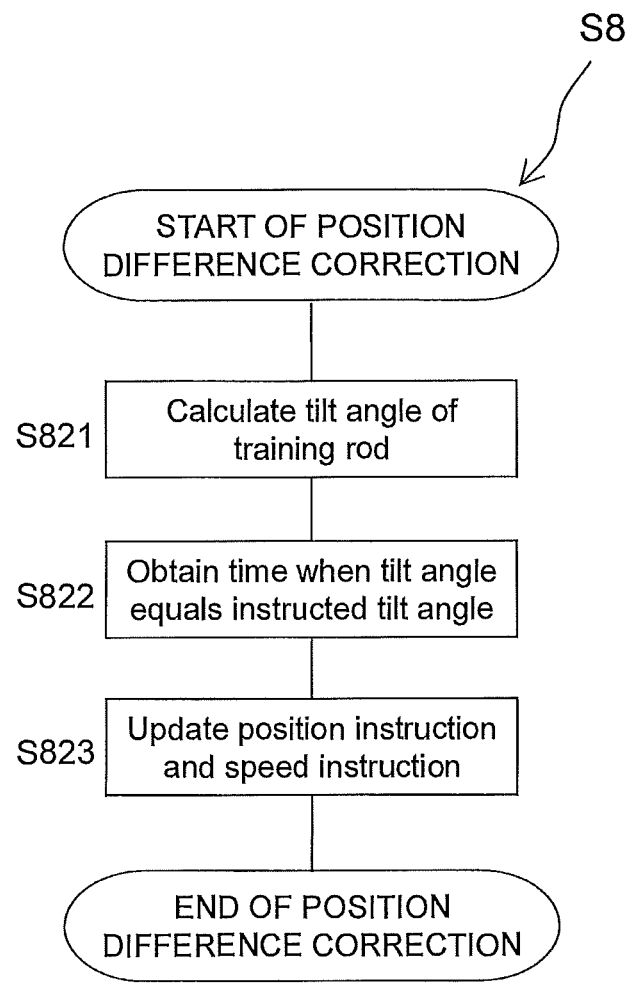
FIG. 14B is a flowchart illustrating an example of a method of resetting the position difference by setting a position difference value as a parameter to zero.
Figure 15A:
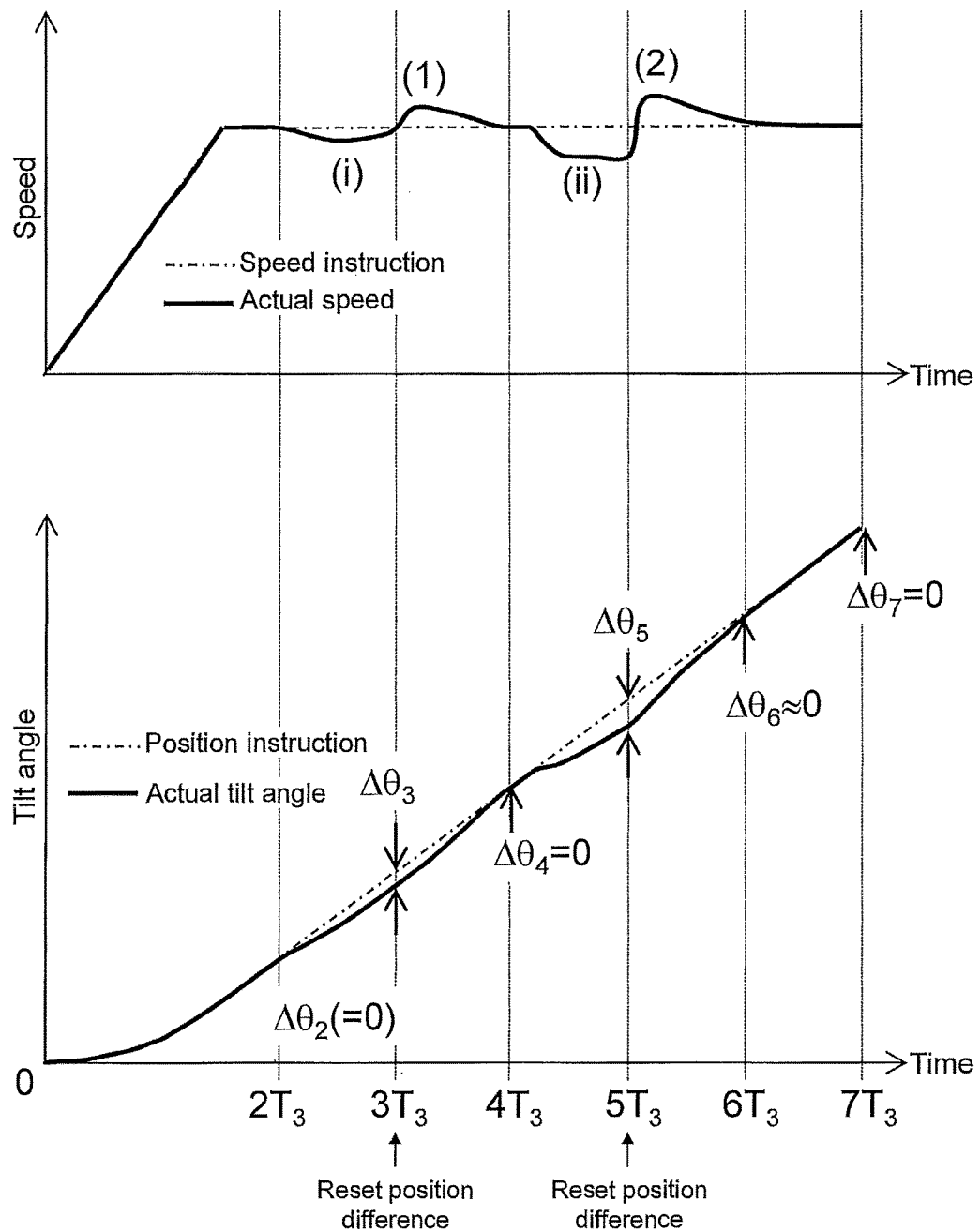
FIG. 15A is a graph schematically illustrating a method of resetting the position difference by the method of physically resetting the position difference.
Figure 15B:
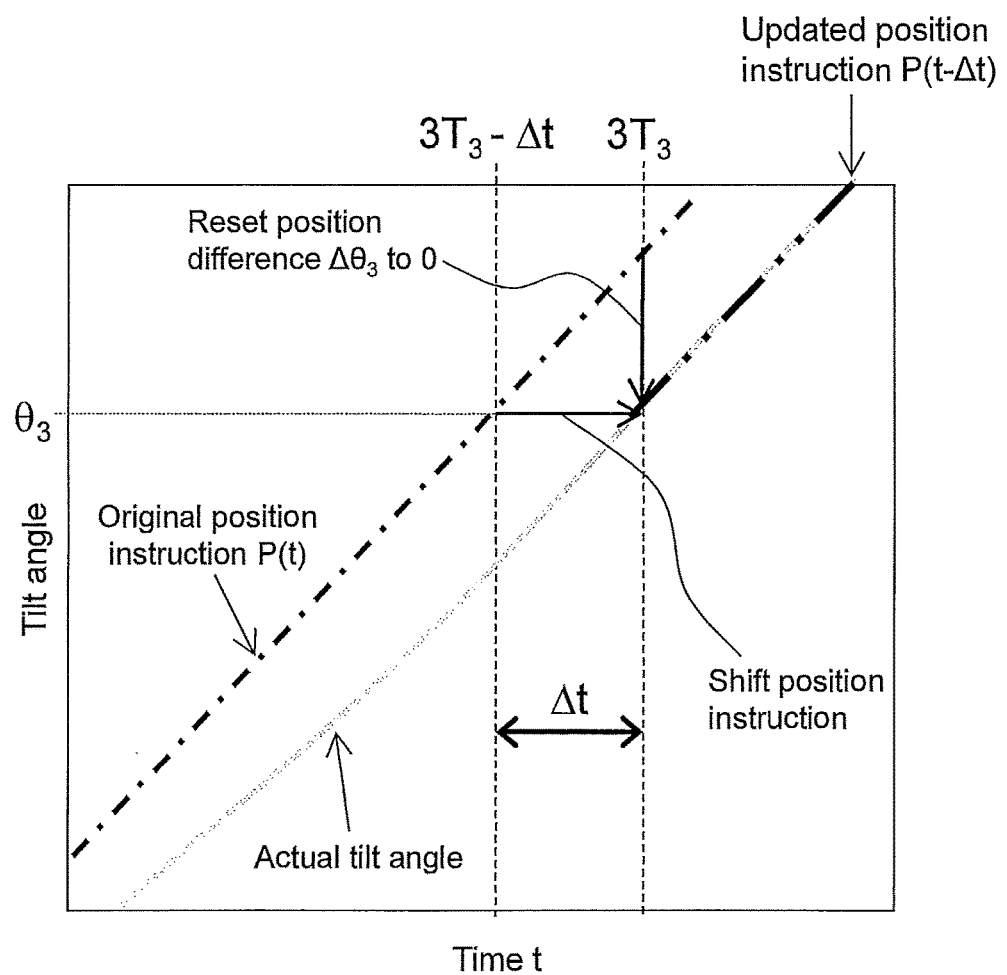
FIG. 15B is a graph schematically illustrating an example of a method of resetting the position difference by setting the position difference value as a parameter to zero.

Next, a method of correcting (resetting) the position difference in Step S8 of the flowchart illustrated in FIG. 9 is described with reference to FIGS. 14A to 15B. FIG. 14A is a flowchart illustrating a method of physically resetting the position difference. FIG. 14B is a flowchart illustrating an example of a method of resetting the position difference by setting the position difference value as a parameter to zero. FIG. 15A is a diagram schematically illustrating a method of resetting the position difference by physically resetting the position difference. FIG. 15B is a diagram schematically illustrating a method of resetting the position difference by setting the position difference value as a parameter to zero.

In Step S8, the position difference eliminating unit 1133 resets the position difference by (i) a method of physically resetting the position difference, and/or (ii) a method of setting the position difference value as a parameter handled by the control unit 11 is set to zero. Hereinafter, each method of resetting the position difference is described.

(i) Method of Physically Resetting Position Difference

First, a method of physically resetting the position difference is described with reference to FIGS. 14A and 15A. Here, "physically" resetting the position difference means to make the actual tilt angle of the training rod 3 equal to the instructed tilt angle of the position instruction.

First, at the timing to perform the correction (reset) of the position difference, the position difference eliminating unit 1133 instructs the switching unit 1135-7 of the motor drive unit 1135 to connect the position control unit 1135-2 to the combining unit 1135-6 in a manner capable of transmitting and receiving signals (Step S811). Further, the switching unit 1135-7 connects the position control unit 1135-2 to the combining unit 1135-6 in a manner capable of transmitting and receiving signals. In this way, the second control amount output from the position control unit 1135-2 can be input to the combining unit 1135-6. Accordingly, the power supply unit 1135-4 can reflect the second control amount when the feedback current or voltage value that is input to the Y-axis direction tilt motor 135a is calculated. As a result, the motor drive unit 1135 can control the Y-axis direction tilt motor 135a so that the tilt angle of the training rod 3 becomes equal to the instructed tilt angle instructed by the position instruction.

Next, the position difference eliminating unit 1133 determines whether or not a correction condition is satisfied (Step S812). Here, the correction condition is a condition for determining whether or not to reflect the second control amount on the control of the Y-axis direction tilt motor 135a. The correction condition may be, for example, whether or not the actual tilt angle of the training rod 3 is equal to the instructed tilt angle (or the position difference is within a predetermined range). When whether or not the actual tilt angle of the training rod 3 is equal to the instructed tilt angle (or the position difference is within a predetermined range) is used as the correction condition, the actual tilt angle of the training rod 3 can be equal to the instructed tilt angle (or can be within a predetermined range).

Other than that, the correction condition may be whether or not a period while the position control unit 1135-2 is connected to the combining unit 1135-6 in Step S811 is a predetermined time period or longer. When whether or not the period while the position control unit 1135-2 is connected to the combining unit 1135-6 is a predetermined time period or longer is used as the correction condition, the actual tilt angle of the training rod 3 can be close to the instructed tilt angle, and at the same time, an excessive increase of the rotation speed of the Y-axis direction tilt motor 135a, which is caused by the second control amount reflected too long on the control of the Y-axis direction tilt motor 135a, can be prevented.

When determining that the correction condition is satisfied ("Yes" in Step S812), the position difference eliminating unit 1133 instructs the switching unit 1135-7 to disconnect between the position control unit 1135-2 and the combining unit 1135-6 (Step S813). As a result, the second control amount is not input to the combining unit 1135-6. Further, the reset of the position difference is finished.

On the other hand, when determining that the correction condition is not satisfied ("No" in Step S812), the position difference eliminating unit 1133 instructs the switching unit 1135-7 to maintain the connection between the position control unit 1135-2 and the combining unit 1135-6. In this way, the reset determination of the accumulated and maintained position difference is continued until the correction condition is satisfied.

The operation of the method of physically resetting the position difference is further described with reference to FIG. 15A. In FIG. 15A, it is supposed that two speed changes (i) and (ii) have occurred. In this case, due to these two speed changes, a position difference $\Delta\theta_3$ is generated at an elapsed time $t=3T_3$, and a position difference $\Delta\theta_5$ is generated at an elapsed time $t=5T_3$.

In Step S7 described above, a case where the timing for resetting the position difference is a timing at which the position difference change amount per the third time period $T_3$ is the second threshold $\phi_2$ or lower is exemplified. Then, if the position difference change amount $\Delta\theta_3-\Delta\theta_2$ at the elapsed time $3T_3$ is the second threshold $\phi_2$ or lower, the second control amount from the position control unit 1135-2 is reflected on the feedback current or voltage input to the Y-axis direction tilt motor 135a by Step S811 described above. As a result, after the elapsed time $3T_3$, the Y-axis direction tilt motor 135a is controlled so that the position difference $\Delta\theta_3$ is eliminated. i.e., the actual tilt angle of the training rod 3 becomes equal to the instructed tilt angle. In this case, the rotation speed of the Y-axis direction tilt motor 135a is temporarily higher than the instructed speed instructed by the speed instruction (speed change (1)). Due to the temporary speed increase as the speed change (1), the position difference $\Delta\theta_3$ is canceled before an elapsed time $4T_3$.

On the other hand, if the position difference change amount $\Delta\theta_5-\Delta\theta_4$ at the elapsed time $5T_3$ is the second threshold $\phi_2$ or lower, and if the correction condition is that the actual tilt angle of the training rod 3 is equal to the instructed tilt angle (the position difference is zero), the position difference $\Delta\theta_5$ generated at the elapsed time $5T_3$ is canceled before an elapsed time $7T_3$ due to the speed change (2) generated when the second control amount is reflected on the input to the Y-axis direction tilt motor 135a. Further, because a position difference $\Delta\theta_6$ is not zero at an elapsed time $6T_3$, the operation of resetting the position difference is continued (namely, the connection state between the position control unit 1135-2 and the combining unit 1135-6 is maintained).

In this way, by continuing the reset determination of the position difference until the correction condition is satisfied, the actual tilt angle of the training rod 3 can be equal (or close) to the instructed tilt angle. For this reason, as illustrated in FIG. 15A, an excessive increase of the accumulated and maintained position difference can be prevented. As a result, when a slow position difference change has continued for a long period of time, an error is not determined, and hence the patient can continue the training of the limb using the training apparatus 100.

Note that it is preferred that a maximum value of the rotation speed of the Y-axis direction tilt motor 135a in the speed changes (1) and (2) be not too large. For instance, the weighting value used for combining the first control amount and the second control amount in the combining unit 1135-6 is optimized (for example, the weighting of the second control amount is decreased), or the control gains $K_{pp}$ and $K_{ip}$ for the position control are set to small values, and hence it is possible to prevent the rotation speed of the Y-axis direction tilt motor 135a from being too large during execution of the position control.

In addition, in the speed changes (1) and (2), the maximum value of the rotation speed of the Y-axis direction tilt motor 135a is suppressed, and hence it is possible to prevent the load applied on the limb by the training rod 3 from being too large.

(ii) Method of Resetting Position Difference by Setting Position Difference Value as a Parameter to Zero Next, a method of resetting the position difference by setting the position difference value as a parameter to zero is described with reference to FIGS. 14B and 15B. Here, a method of resetting the position difference at the elapsed time $3T_3$ in FIG. 15A is exemplified and described.

First, an actual tilt angle of the training rod 3 at the timing at which the position difference eliminating unit 1133 resets the accumulated and maintained position difference is calculated (Step S821). In the position difference eliminating unit 1133, the actual tilt angle of the training rod 3 at the elapsed time $3T_3$ is $\theta_3$.

Next, the position difference eliminating unit 1133 obtains the time point when the instructed tilt angle indicated by the position instruction becomes $\theta_3$ from the position instruction (Step S822). It is supposed that the position instruction is expressed by a function P(t), and then the time point t in the position instruction when the instructed tilt angle becomes $\theta_3$ is $3T_3-\Delta t$ (namely, $P(3T_3-\Delta t)=\theta_3$). Further, the position difference eliminating unit 1133 calculates the difference $\Delta t$ between the time point when the instructed tilt angle in the position instruction becomes $\theta_3$ and the time point when the tilt angle of the training rod 3 actually becomes $\theta_3$.

Next, the position difference eliminating unit 1133 updates the function P(t) of the position instruction (Step S823). In Step S823, the function P(t) of the position instruction is converted from the function P(t) to the function $P(t-\Delta t)$ at the elapsed time $3T_3$ so as to be updated. This means that in FIG. 15B, at the elapsed time $3T_3$, the function P(t) of the position instruction (the position instruction illustrated by a dot-dashed line in FIG. 15B) is moved in parallel behind by $\Delta t$ on the time axis (to the right in FIG. 15B) (to be the position instruction illustrated by a double dot-dashed line in FIG. 15B). Further, at the elapsed time $3T_3$, the instructed tilt angle indicated in the position instruction is $P(3T_3-\Delta t)$, namely $\theta_3$. As a result, the difference (the position difference) between the actual tilt angle of the training rod 3 and the instructed tilt angle becomes zero.

Further, as illustrated in FIG. 15B, when setting the position difference as a parameter to zero so as to reset the position difference, the position difference between the actual tilt angle of the training rod 3 and the instructed tilt angle indicated in the last position instruction P(t) is accumulated as it is and is maintained.

Figure 15C:
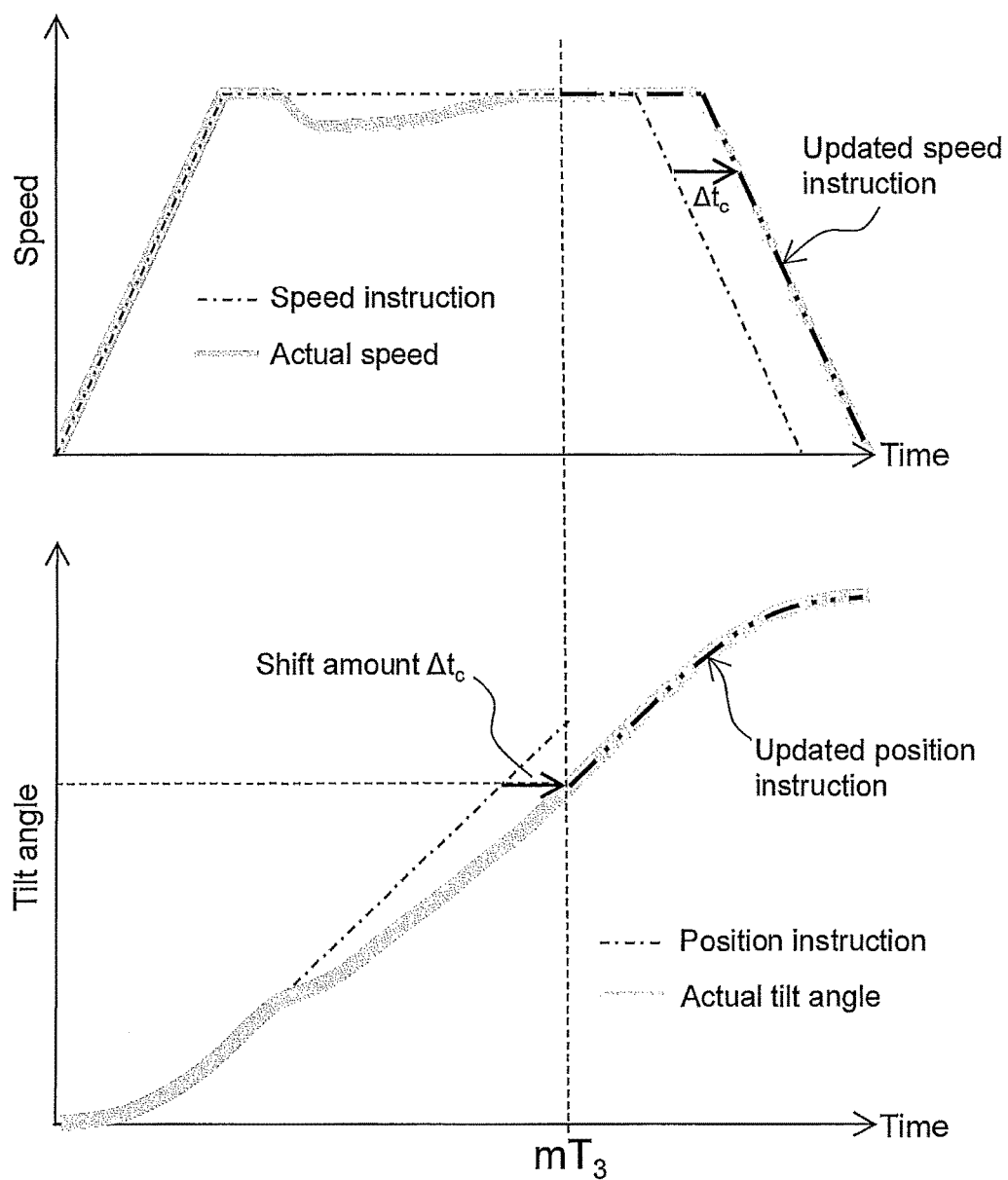
FIG. 15C is a graph schematically illustrating a manner in which when the position instruction is shifted in parallel with respect to the time axis, the speed instruction is also shifted in parallel with respect to the time axis.

In addition, when the function P(t) of the position instruction is updated to $P(t-\Delta t)$, a function V(t) of the speed instruction is also updated to $V(t-\Delta t)$. For instance, as illustrated in FIG. 15C, when the function P(t) of the position instruction is updated to a function $P(t-\Delta t_c)$ (a position instruction illustrated by a double dot-dashed line in FIG. 15C) at an elapsed time $mT_3$ (m is an integer), the updated speed instruction $V(t-\Delta t_c)$ (a speed instruction illustrated by a double dot-dashed line in FIG. 15C) corresponds to a function obtained by moving the speed instruction V(t) before the update in parallel behind by $\Delta t_c$ on the time axis. In this way, the reaching time is delayed by $\Delta t_c$, but the position instruction appropriately corresponds to the speed instruction in a temporal manner. As a result, the motor control unit 113a can control the Y-axis direction tilt motor 135a so that the training rod 3 can accurately reach the target tilt angle with a difference as small as possible.

In addition, in the method of resetting the position difference as a parameter to zero, the motor control unit 113a does not perform the position control for physically canceling the position difference. For this reason, the tilt angle of the training rod 3 per unit time does not exceed the instructed speed instructed by the speed instruction. As a result, the training can be safely continued.

(6) Effects of this Embodiment

Hereinafter, effects of this embodiment are described.

The training apparatus 100 (an example of the training apparatus) is a training apparatus for training an upper limb and/or a lower limb of a patient (an example of the patient) in accordance with a training program (an example of the training program). The training apparatus 100 includes the fixed frame 1 (an example of the fixed frame), the training rod 3 (an example of the training rod), the X-axis direction tilt motor 135b (an example of the motor), the Y-axis direction tilt motor 135a (an example of the motor), the second rotation information detection sensor 135b-1 (an example of the rotation information detection sensor), the first rotation information detection sensor 135a-1 (an example of the rotation information detection sensor), the tilt angle calculation unit 1131 (an example of the tilt angle calculation unit), the position difference calculation unit 1132 (an example of the position difference calculation unit), the determination unit 1134 (an example of the determination unit), the motor drive unit 1135 (an example of the motor drive unit), and the position difference eliminating unit 1133 (an example of the position difference eliminating unit). The fixed frame 1 is placed on or in the vicinity of a floor. The training rod 3 is supported by the fixed frame 1 in a manner capable of tilting about at least the X-axis or the Y-axis (an example of the predetermined tilting axis). In addition, the training rod 3 holds the limb (an example of the limb). The X-axis direction tilt motor 135b and the Y-axis direction tilt motor 135a tilt the training rod 3 about the X-axis and the Y-axis, respectively. The first rotation information detection sensor 135a-1 and the second rotation information detection sensor 135b-1 output an amount of rotation of the Y-axis direction tilt motor 135a and an amount of rotation of the X-axis direction tilt motor 135b, respectively. The tilt angle calculation unit 1131 calculates a tilt angle of the training rod 3 (an example of the tilt angle) on the basis of the amount of rotation of the X-axis direction tilt motor 135b and the amount of rotation of the Y-axis direction tilt motor 135a. The position difference calculation unit 1132 calculates the position difference (an example of the position difference) at the interval of the first time period $T_1$ (an example of the first time period). The determination unit 1134 obtains the position difference calculated by the position difference calculation unit 1132 every time when the second time period $T_2$ (an example of the second time period) elapses. Further, the determination unit 1134 determines whether or not the position difference change amount generated in the second time period $T_2$ is the first threshold $\phi_1$ (an example of the first threshold) or lower. When the determination unit 1134 determines that the position difference change amount generated in the second time period $T_2$ is the first threshold $\phi_1$ or lower, the motor drive unit 1135 drives the X-axis direction tilt motor 135b and the Y-axis direction tilt motor 135a so that the position difference is accumulated and maintained. The position difference eliminating unit 1133 resets the accumulated and maintained position difference at the preset timing.

In the training apparatus 100, the determination unit 1134 first obtains the position difference every time when the unit time (the second time period $T_2$) elapses. Next, the determination unit 1134 calculates the position difference change amount generated in the second time period $T_2$. Further, the determination unit 1134 determines whether or not the position difference change amount generated in the second time period $T_2$ is the first threshold $\phi_1$ or lower.

When the determination unit 1134 determines that the position difference change amount generated in the second time period $T_2$ is the first threshold $\phi_1$ or lower, the motor drive unit 1135 drives one of the X-axis direction tilt motor 135b and the Y-axis direction tilt motor 135a so that the position difference is accumulated and maintained. Further, the position difference eliminating unit 1133 resets the accumulated and maintained position difference at the preset timing while the X-axis direction tilt motor 135b and the Y-axis direction tilt motor 135a are driven.

In this way, the determination unit 1134 obtains the position difference every time when the unit time (second time period $T_2$) elapses. In this way, the position difference change amount generated in the unit time (second time period $T_2$) can be calculated. In addition, the determination unit 1134 determines whether or not the position difference change amount generated in the unit time (second time period $T_2$) is the first threshold $\phi_1$ or lower. In this way, the determination unit 1134 can appropriately determine the case where the following status in which the position difference is not zero but is not changed has occurred, or the case where the following status in which the position difference gradually changes has occurred.

Further, the position difference eliminating unit 1133 resets the accumulated and maintained position difference at the predetermined timing. In this way, it is avoided that the determination unit 1134 determines an error when the position difference generated in the state where the position difference is not zero but is not changed, or the position difference generated in the state where the position difference gradually changes is increased. As a result, the patient can continue the training of the limb with the training apparatus 100.

The training rod 3 may be expandable and contractible in the longitudinal direction (an example of the longitudinal axis direction). When the training rod 3 is expandable and contractible in the longitudinal axis direction, it is possible to carry out the training of an upper limb or a lower limb (limb) in the longitudinal direction of the training rod 3.

If the position difference change amount generated in the second time period $T_2$ is higher than the first threshold $\phi_1$, the determination unit 1134 determines an error. In this way, it is possible to predict a potential abnormality in the training apparatus 100, and/or, a potential obstacle that may affect continuation of the training, so as to appropriately determine that the limb cannot follow the training program.

The training apparatus 100 further includes the training instruction unit 5 (an example of the information providing unit). When the determination unit 1134 determines that an error has occurred, the training instruction unit 5 provides the user with visual or auditory information.

In this way, it is possible to inform the user of the status of the training apparatus and/or a potential obstacle that may affect continuation of the training.

When the patient has moved the training rod 3 to reach the target tilt angle (an example of the passing point preset in the training route set by the training program), the training instruction unit 5 provides the user with information. In this way, the user can know that the training rod 3 has been operated just in accordance with the training program. In addition, because the user is provided with the visual or auditory information when the patient has moved the training rod 3 to reach the target tilt angle, the patient can maintain motivation to continue the training.

When the determination unit 1134 determines that an error has occurred, the X-axis direction tilt motor 135b, the Y-axis direction tilt motor 135a, and the expansion/contraction motor 359 (an example of the motor) may be stopped. In this way, when an error has occurred, i.e., when it is determined that there is a potential obstacle that may affect continuation of the training, the training apparatus 100 can be safely stopped.

The determination unit 1134 further obtains the position difference every time when the third time period $T_3$ (an example of the third time period) elapses. Further, the determination unit 1134 determines whether or not the position difference change amount generated in the third time period $T_3$ is the second threshold $\phi_2$ (an example of the second threshold) or lower. Further, when the determination unit 1134 determines that the position difference change amount generated in the third time period $T_3$ is the second threshold $\phi_2$ or lower, the position difference eliminating unit 1133 resets the accumulated and maintained position difference.

In this way, the accumulated and maintained position difference can be reset without always controlling the X-axis direction tilt motor 135b, the Y-axis direction tilt motor 135a, and/or the expansion/contraction motor 359 (the position control) so that the actual tilt angle of the training rod 3 follows the tilt angle instructed by the training program (the instructed tilt angle), and the patient can continue the training.

The position difference eliminating unit 1133 resets the accumulated and maintained position difference when the operation of the training rod 3 is stopped. In this way, the position difference generated in the training this time is not carried over to the next training and after, and hence the patient can continue the training.

The training apparatus 100 further includes the instruction generation unit 111 (an example of the instruction generation unit). The instruction generation unit 111 generates the speed instruction (an example of the speed instruction) including at least the acceleration instruction (an example of the acceleration instruction) for accelerating the X-axis direction tilt motor 135b, the Y-axis direction tilt motor 135a, and/or the expansion/contraction motor 359 in accordance with the preset training program, and the deceleration instruction (an example of the deceleration instruction) for decelerating the motors. In this case, the motor drive unit 1135 controls the motor so as to follow only the speed instruction when the acceleration instruction is executed.

Because the speed instruction including at least the acceleration instruction and the deceleration instruction is used for driving the motor, the motor can be smoothly operated. As a result, the patient can operate the training rod 3 as intended.

In addition, because the motor drive unit 1135 drives the motor so as to follow only the speed instruction when the acceleration instruction is executed, the motor control can be performed so that the position difference is accumulated and maintained. As a result, even if a relatively large motor torque is required and a position difference is apt to occur, for example, even if the training rod 3 is operated at a large tilt angle, the patient can continue the training of the limb using the training apparatus 100. Further, because the position difference is accumulated and maintained, a state of the limb during the training can be grasped on the basis of the accumulated and maintained amount of the position difference.

The speed instruction includes at least the acceleration instruction and the deceleration instruction, and can further include the constant speed instruction for rotating the motor at a constant speed. In this case, the motor drive unit 1135 controls the motor so as to further follow only the speed instruction when the constant speed instruction is executed.

Because the speed instruction further includes the constant speed instruction, the motor can be smoothly operated at a constant speed on the basis of the feedback current from the motor even if the training rod 3 is operated at a large tilt angle. In addition, because the motor drive unit 1135 controls the motor so as to follow only the speed instruction when the constant speed instruction is executed, the motor control can be performed so that the position difference is accumulated and maintained. As a result, even if a relatively large motor torque is required and a position difference is apt to occur, for example, even if the training rod 3 is operated at a large tilt angle, the patient can continue the training of the limb using the training apparatus 100. In addition, when the motor is rotated at a constant speed, the training of the limb can be continued by a constant speed movement. Further, because the position difference is accumulated and maintained, a state of the limb of the patient during the training can be grasped on the basis of the accumulated and maintained amount of the position difference.

The instruction generation unit 111 further generates the position instruction (an example of the position instruction) for controlling the tilt angle of the training rod 3 in accordance with the training program. In addition, the motor drive unit 1135 controls the motor so as to follow the speed instruction and the position instruction when the deceleration instruction is executed.

In this way, the motor drive unit 1135 can control the motor so that the training rod 3 can reach the target tilt angle instructed by the training program with a difference as small as possible. As a result, when the position information of the training rod 3 is fed back as the visual information to the patient, for example, this position information can be appropriately used.

The position difference eliminating unit 1133 resets the accumulated and maintained position difference when the deceleration instruction is started. In this way, when the deceleration instruction is executed, the rotation speed of the motor can be prevented from being excessively increased by the position instruction.

2. Other Embodiments

Although an embodiment of the present invention is described above, the present invention is not limited to the embodiment but can be modified variously within the scope of the spirit of the invention. In particular, a plurality of embodiments and variations described in this specification can be arbitrarily combined as necessary.

(A) Another Embodiment Concerning Motor Control

In the first embodiment described above, only when the deceleration instruction of the speed instruction is executed, the Y-axis direction tilt motor 135a (the X-axis direction tilt motor 135b or the expansion/contraction motor 359) is controlled so that the tilt angle of the training rod 3 follows the instructed tilt angle instructed by the position instruction (position control). However, this is not a limitation. Also when the acceleration instruction of the speed instruction is executed and/or when the constant speed instruction is executed, the Y-axis direction tilt motor 135a (the X-axis direction tilt motor 135b or the expansion/contraction motor 359) may be controlled by the position control and the speed control. In this case, the switching unit 1135-7 of the motor drive unit 1135 is not necessary in particular.

When the acceleration instruction of the speed instruction is executed and/or when the constant speed instruction is executed, if the Y-axis direction tilt motor 135a (the X-axis direction tilt motor 135b or the expansion/contraction motor 359) is controlled by the position control, it is preferred to adjust the control gains $K_{pp}$ and $K_{ip}$ or to adjust the weighting value of the second control amount of the combining unit 1135-6 so that the tilt angle speed of the training rod 3 does not become excessively large.

In this way, the tilt angle of the training rod 3 can follow the instructed tilt angle without excessively increasing the tilt angle speed of the training rod 3.

INDUSTRIAL APPLICABILITY

The present invention can be widely applied to a training apparatus including a training rod driven by a motor, for carrying out training of a limb of a patient in accordance with a predetermined training program.

REFERENCE SIGNS LIST 100 training apparatus
1 fixed frame
11 control unit
111 instruction generation unit
113a, 113b, 113c motor control unit
1131 tilt angle calculation unit
1132 position difference calculation unit
1133 position difference eliminating unit
1134 determination unit
1135 motor drive unit
1135-1 speed control unit
1135-2 position control unit
1135-3 speed calculation unit
1135-4 power supply unit
1135-5 difference calculation unit
1135-6 combining unit
1135-7 switching unit
13 training rod tilt mechanism
131 X-axis direction tilt member
131a, 131b shaft
133 Y-axis direction tilt member
133a, 133b shaft
135a Y-axis direction tilt motor
135a-1 first rotation information detection sensor
135b X-axis direction tilt motor
135b-1 second rotation information detection sensor
15a, 15b training rod tilt mechanism fixing member
3 training rod
31 limb support member
33 fixed stay
35 expansion/contraction mechanism
351 movable stay
353 cover
355 nut
357 threaded shaft
359 expansion/contraction motor
359-1 third rotation information detection sensor
37 guide rail
5 training instruction unit
7 fixing member
9 chair
91 chair connecting member
$K_{pv}$, $K_{iv}$ control gain in speed control
$K_{pp}K_{ip}$ control gain in position control
P(t) position instruction
V(t) speed instruction
S, S' space
$T_1$ first time period
$T_2$ second time period
$T_3$ third time period
m, n integer
t, $t_1$, $t_2$, $t_3$, $t_4$, $t_5$, $t_a$, $t_b$ elapsed time
$\Delta t$, $\Delta t_c$ time shift amount of position instruction
$\Delta v$ speed difference
$\theta_d$ deceleration start position (tilt angle corresponding to deceleration start position)
$\Delta \theta_A$, $\Delta \theta_B$, $\Delta \theta_n$, $\Delta \theta_{n-1}$, $\Delta \theta_2$, $\Delta \theta_3$, $\Delta \theta_4$, $\Delta \theta_5$, $\Delta \theta_6$, $\Delta \theta_7$ position difference
$\Delta \Theta_{n-1}$, $\Delta \Theta_n$ position difference
$\phi_i$ first threshold
$\phi_2$ second threshold

The invention claimed is:

1. A training apparatus for training upper and/or lower limbs of a user in accordance with a predetermined training program, the training apparatus comprising:
    a fixed frame placed on or in the vicinity of a floor;
    a training rod supported by the fixed frame in a manner capable of tilting about a predetermined tilting axis with at least one degree of freedom, so as to hold a limb;
    a motor configured to tilt the training rod about the tilting axis;
    a rotation information detection sensor configured to output an amount of rotation of the motor;
    a tilt angle calculation unit configured to calculate a tilt angle of the training rod on the basis of the amount of rotation of the motor;
    a position difference calculation unit configured to calculate a position difference at an interval of a predetermined first time period, the position difference being a difference between an actual tilt angle of the training rod and an instructed tilt angle of the training rod instructed by the training program;
    a determination unit configured to obtain the position difference calculated by the position difference calculation unit every time when a predetermined second time period elapses, and to determine whether or not a position difference change amount generated in the second time period is a first threshold or lower;
    a motor drive unit configured to drive the motor so that the position difference is accumulated and maintained if the determination unit determines that the position difference change amount generated in the second time period is the first threshold or lower; and
    a position difference eliminating unit configured to reset the accumulated and maintained position difference at a preset timing.

2. The training apparatus according to claim 1, wherein the training rod is capable of expanding and contracting in a longitudinal axis direction.

3. The training apparatus according to claim 1, wherein the determination unit determines an error if the position difference change amount generated in the second time period is higher than the first threshold.

4. The training apparatus according to claim 3, further comprising an information providing unit configured to provide the user with visual or auditory information when the determination unit determines that an error has occurred.

5. The training apparatus according to claim 4, wherein the information providing unit provides the user with the visual or auditory information when the user has moved the training rod to reach a preset passing point in a training route set by the training program.

6. The training apparatus according to claim 3, wherein rotation of the motor is stopped when the determination unit determines that an error has occurred.

7. The training apparatus according to claim 1, wherein
the determination unit further obtains the position difference every time when a third time period elapses, and determines whether or not the position difference change amount generated in the third time period is a second threshold or lower, and
if the determination unit determines that the position difference change amount generated in the third time period is the second threshold or lower, the position difference eliminating unit resets the accumulated and maintained position difference.

8. The training apparatus according to claim 1, wherein the position difference eliminating unit resets the accumulated and maintained position difference when operation of the training rod is stopped.

9. The training apparatus according to claim 1, further comprising an instruction generation unit configured to generate a speed instruction including at least an acceleration instruction for accelerating the motor and a deceleration instruction for decelerating the motor in accordance with the training program, wherein
the motor drive unit controls the motor so as to follow only the speed instruction when the acceleration instruction is executed.

10. The training apparatus according to claim 9, wherein the speed instruction further includes a constant speed instruction for rotating the motor at a constant speed between the acceleration instruction and the deceleration instruction, and the motor drive unit further controls the motor so as to follow only the speed instruction when the constant speed instruction is executed.

11. The training apparatus according to claim 9, wherein
the instruction generation unit further generates a position instruction for controlling the tilt angle of the training rod in accordance with the training program, and
the motor drive unit controls the motor so as to follow the speed instruction and the position instruction when the deceleration instruction is executed.

12. The training apparatus according to claim 9, wherein the position difference eliminating unit resets the accumulated and maintained position difference when the deceleration instruction is started.

* * * * *